US012768831B1

(12) United States Patent
Shultz et al.

(10) Patent No.: US 12,768,831 B1
(45) Date of Patent: Oct. 20, 2026

(54) MODEL OF FUNCTIONS AND REGULATION OF HUMAN NATURAL KILLER CELLS

(71) Applicants: The Jackson Laboratory, Bar Harbor, ME (US); University of Massachusetts, Westborough, MA (US)

(72) Inventors: Leonard D. Shultz, Bar Harbor, ME (US); Michael A. Brehm, Westborough, MA (US); Dale L. Greiner, Westborough, MA (US)

(73) Assignees: The Jackson Laboratory, Bar Harbor, ME (US); University of Massachusetts, Westborough, MA (US)

( * ) Notice: Subject to any disclaimer, the term of this patent is extended or adjusted under 35 U.S.C. 154(b) by 0 days.

(21) Appl. No.: 19/250,234

(22) Filed: Jun. 26, 2025

Related U.S. Application Data

(63) Continuation of application No. 16/637,621, filed as application No. PCT/US2018/046021 on Aug. 9, 2018, now abandoned.

(60) Provisional application No. 62/554,818, filed on Sep. 6, 2017, provisional application No. 62/543,218, filed on Aug. 9, 2017.

(51) Int. Cl.

| | |
|---|---|
| ***G01N 33/00*** | (2006.01) |
| ***A01K 67/0276*** | (2024.01) |
| ***A01K 67/0278*** | (2024.01) |
| ***G01N 33/50*** | (2006.01) |

(52) U.S. Cl.
CPC ...... *G01N 33/5011* (2013.01); *A01K 67/0276* (2013.01); *A01K 67/0278* (2013.01); *G01N 33/5073* (2013.01); *A01K 2217/15* (2013.01); *A01K 2227/105* (2013.01); *A01K 2267/0331* (2013.01); *G01N 2500/10* (2013.01); *G01N 2800/7028* (2013.01)

(58) Field of Classification Search
CPC ........... G01N 33/5011; G01N 33/5073; G01N 2500/10; G01N 2800/7028; A01K 67/0276; A01K 67/0278; A01K 2217/15; A01K 2227/105; A01K 2267/0331
See application file for complete search history.

(56) References Cited

U.S. PATENT DOCUMENTS

| | | | | |
|---|---|---|---|---|
| 12,409,237 | B1 | 9/2025 | Shultz et al. | |
| 2020/0236916 | A1 * | 7/2020 | Shultz | A01K 67/0275 |
| 2025/0212854 | A1 | 7/2025 | Shultz | |
| 2026/0033467 | A1 | 2/2026 | Shultz et al. | |

FOREIGN PATENT DOCUMENTS

| | | | |
|---|---|---|---|
| EP | 3861854 | A1 | 8/2021 |

OTHER PUBLICATIONS

The Jackson Laboratory Stock No. 001976 (Jan. 2026 downloaded). (Year: 2026).*

Allen et al., Humanized immune system mouse models: progress, challenges and opportunities. Nat Immunol. Jul. 2019;20(7):770-774. doi: 10.1038/s41590-019-0416-z.

Doloff et al., Identification of a humanized mouse model for functional testing of immune-mediated biomaterial foreign body response. Sci Adv. Jun. 16, 2023;9(24):eade9488. doi: 10.1126/sciadv.ade9488. Epub Jun. 16, 2023.

Takai et al., FcR gamma chain deletion results in pleiotrophic effector cell defects. Cell. Feb. 11, 1994;76(3):519-29. doi: 10.1016/0092-8674(94)90115-5.

Tonomura et al., Pig islet xenograft rejection in a mouse model with an established human immune system. Xenotransplantation. Mar.-Apr. 2008;15(2):129-35. doi: 10.1111/j.1399-3089.2008.00450.x.

Wang et al., Humanized mouse model for assessing the human immune response to xenogeneic and allogeneic decellularized biomaterials. Biomaterials. Jun. 2017;129:98-110. doi: 10.1016/j.biomaterials.2017.03.016. Epub Mar. 11, 2017. Author Manuscript, 24 pages.

Yachen et al., Generation of a new strain of NOD/SCID/IL2Ry-/- mice with targeted disruption of Prkdc and IL2Ry genes using CRISPR/Cas9 system. Journal of Southern Medical University. Jun. 2, 20180;38(6):639-646. doi: 10.3969/j.issn.1673-4254.2018.06.01.

* cited by examiner

*Primary Examiner* — Lei Yao
(74) *Attorney, Agent, or Firm* — Wolf, Greenfield & Sacks, P.C.

(57) ABSTRACT

Methods provided according to aspects of the present disclosure have various utilities such as in vivo testing of substances directed against human cancer.

20 Claims, 17 Drawing Sheets

Specification includes a Sequence Listing.

MODEL OF FUNCTIONS AND REGULATION OF HUMAN NATURAL KILLER CELLS

REFERENCE TO RELATED APPLICATIONS

This application is a continuation of U.S. application Ser. No. 16/637,621, filed Feb. 7, 2020 is a national stage filing under 35 U.S.C. § 371 of international application number PCT/US2018/046021, filed Aug. 9, 2018, which was published under PCT Article 21 (2) in English and claims the benefit under 35 U.S.C. § 119 (e) of U.S. provisional patent application No. 62/543,218, filed Aug. 9, 2017 and U.S. provisional patent application No. 62/554,818, filed Sep. 6, 2017, each of which is incorporated herein by reference in its entirety.

REFERENCE TO AN ELECTRONIC SEQUENCE LISTING

The content of the electronic sequence listing (J022770047US03-SEQ-HJD.xml; Size: 3,161 bytes; and Date of Creation: Jun. 25, 2025) is herein incorporated by reference in its entirety.

BACKGROUND OF THE INVENTION

IL-15 is produced by multiple cell types including bone marrow stromal cells. The activity of IL-15 has been reported to be increased when the IL-15 secreting cell expresses IL-15 receptor alpha (IL-15rα). The IL-15: IL-15rα complex is transpresented to NK cells and other IL-15 responsive cells. Human NK cells mediate antibody-dependent cell-mediated cytotoxicity (ADCC) against human tumors in vivo. There is a continuing need for mouse models of functions and regulation of human natural killer (NK) cells and other interleukin 15 (IL-15)-dependent cell populations and processes in studies of human immunity, cancer, infectious diseases, and other areas. However, it has been difficult to study the in vivo role of human NK cells in cancer immunotherapy because of the lack of human IL-15. Human IL-15 is required for the development and survival in vivo of mature human functional NK cells and mouse IL-15 will not support human NK cell development. As shown herein, unexpectedly, immunodeficient mice expressing human IL-15 support human NK cell development without the need to supply IL-15rα or any other factors. An immunodeficient mouse expressing human IL-15 of the present invention provides a model system for assessment of NK-cell mediated ADCC mouse, a model of function and regulation of human natural killer (NK) cells and other interleukin 15 (IL-15)-dependent cell populations and processes in studies of human immunity, cancer, infectious diseases, and other areas.

SUMMARY OF THE INVENTION

Methods provided according to aspects of the present invention have various utilities such as, in vivo testing of substances directed against human cancer.

Assaying a response of a xenogeneic tumor and/or tumor cells to the test substance includes comparing the response to a standard to determine the effect of the test substance on the xenogeneic tumor cells according to aspects of methods of the present invention, wherein an inhibitory effect of the test substance on the xenogeneic tumor cells identifies the test substance as an anti-tumor composition.

According to aspects of the present invention, a test substance is an anti-cancer agent. According to aspects of the present invention, the test substance is an anti-cancer immunotherapeutic, such as an anti-cancer antibody or antigen binding fragment thereof.

According to aspects of the present invention, a test substance is a chemotherapeutic agent or an immunotherapeutic agent. According to aspects of the present invention, a test substance can specifically binds PD-1, PD-L1, or CTLA-4. According to aspects of the present invention, a test substance can be an immune checkpoint inhibitor such as a PD-1 inhibitor, PD-L1 inhibitor, or CTLA-4 inhibitor. According to aspects of the present invention, a test substance is an immune checkpoint inhibitor selected from atezolizumab, avelumab, durvalumab, ipilimumab, nivolumab, pembrolizumab, and an antigen-binding fragment of any one of the foregoing.

The test substance can be administered by any suitable route of administration, such as, but not limited to, oral, rectal, buccal, nasal, intramuscular, vaginal, ocular, otic, subcutaneous, transdermal, intratumoral, intravenous, and intraperitoneal.

Methods for identifying anti-tumor activity of a test substance according to aspects of the present invention include providing an immunodeficient hu-IL-15 mouse; administering xenogeneic tumor cells to the immunodeficient hu-IL-15 mouse, wherein the xenogeneic tumor cells form a solid or non-solid tumor in the immunodeficient hu-IL-15 mouse; administering a test substance to the immunodeficient hu-IL-15 mouse; assaying a response of the xenogeneic tumor and/or tumor cells to the test substance, wherein an inhibitory effect of the test substance on the tumor and/or tumor cells identifies the test substance as having anti-tumor activity.

Methods for identifying anti-tumor activity of a test substance according to aspects of the present invention include providing an immunodeficient hu-IL-15 mouse, wherein the immunodeficient hu-IL-15 mouse has engrafted xenogeneic HSC; administering xenogeneic tumor cells to the immunodeficient hu-IL-15 mouse, wherein the xenogeneic tumor cells form a solid or non-solid tumor in the immunodeficient hu-IL-15 mouse; administering a test substance to the immunodeficient hu-IL-15 mouse; assaying a response of the xenogeneic tumor and/or tumor cells to the test substance, wherein an inhibitory effect of the test substance on the tumor and/or tumor cells identifies the test substance as having anti-tumor activity.

Methods for identifying anti-tumor activity of a test substance according to aspects of the present invention include providing an immunodeficient hu-IL-15 mouse, wherein the immunodeficient hu-IL-15 mouse has engrafted human HSC; administering human tumor cells to the immunodeficient hu-IL-15 mouse, wherein the human tumor cells form a solid or non-solid tumor in the immunodeficient hu-IL-15 mouse; administering a test substance to the immunodeficient hu-IL-15 mouse; assaying a response of the human tumor and/or tumor cells to the test substance, wherein an inhibitory effect of the test substance on the tumor and/or tumor cells identifies the test substance as having anti-tumor activity.

A method of identifying anti-tumor activity of a test substance is provided according to aspects of the present invention which includes providing an immunodeficient mouse genetically modified to include a nucleotide sequence encoding hu-IL-15 in its genome is provided according to aspects of the present invention, wherein the mouse expresses the hu-IL-15; administering human tumor cells to the immunodeficient mouse, wherein the human tumor cells form a solid or non-solid tumor in the genetically-modified, immunodeficient mouse; administering a test substance to the immunodeficient mouse; and assaying a response of the solid or non-solid tumor to the test substance, wherein an inhibitory effect of the test substance on the tumor and/or tumor cells identifies the test substance as having anti-tumor activity. According to particular aspects, the immunodeficient mouse genetically modified to include a nucleotide sequence encoding hu-IL-15 in its genome, wherein the mouse expresses the hu-IL-15, is characterized by absence of functional endogenous mouse NK cells and the method includes administering human tumor cells to the immunodeficient mouse, wherein the human tumor cells form a solid or non-solid tumor in the genetically-modified, immunodeficient mouse; administering a test substance to the immunodeficient mouse; and assaying a response of the solid or non-solid tumor to the test substance, wherein an inhibitory effect of the test substance on the tumor and/or tumor cells identifies the test substance as having anti-tumor activity. According to particular aspects, the immunodeficient mouse genetically modified to include a nucleotide sequence encoding hu-IL-15 in its genome, wherein the mouse expresses the hu-IL-15, is IL-2RG null such that it lacks a functional endogenous IL-2RG gene and is characterized by absence of functional endogenous mouse NK cells and the method includes administering human tumor cells to the immunodeficient mouse, wherein the human tumor cells form a solid or non-solid tumor in the genetically-modified, immunodeficient mouse; administering a test substance to the immunodeficient mouse; and assaying a response of the solid or non-solid tumor to the test substance, wherein an inhibitory effect of the test substance on the tumor and/or tumor cells identifies the test substance as having anti-tumor activity. According to particular aspects, the immunodeficient mouse genetically modified to include a nucleotide sequence encoding hu-IL-15 in its genome, wherein the mouse expresses the hu-IL-15, is a genetically modified NSG, NRG or NOG mouse characterized by absence of functional endogenous mouse NK cells and wherein the mouse further includes human NK cell line cells and/or human natural killer cells wherein the human natural killer cells are produced in the mouse by differentiation of human hematopoietic stem cells in the mouse and/or by administration of PBMCs including human natural killer cells, and/or by administration of purified human NK cells, and the method includes administering human tumor cells to the immunodeficient mouse, wherein the human tumor cells form a solid or non-solid tumor in the genetically-modified, immunodeficient mouse; administering a test substance to the immunodeficient mouse; and assaying a response of the solid or non-solid tumor to the test substance, wherein an inhibitory effect of the test substance on the tumor and/or tumor cells identifies the test substance as having anti-tumor activity.

According to particular aspects, the immunodeficient mouse genetically modified to include a nucleotide sequence encoding hu-IL-15 in its genome, wherein the mouse expresses the hu-IL-15, is IL-2RG null such that it lacks a functional endogenous IL-2RG gene, is characterized by absence of functional endogenous mouse NK cells, wherein the mouse further includes human NK cell line cells and/or human natural killer cells wherein the human natural killer cells are produced in the mouse by differentiation of human hematopoietic stem cells in the mouse and/or by administration of PBMCs including human natural killer cells, and/or by administration of purified human NK cells, and the method includes administering human tumor cells to the immunodeficient mouse, wherein the human tumor cells form a solid or non-solid tumor in the genetically-modified, immunodeficient mouse; administering a test substance to the immunodeficient mouse; and assaying a response of the solid or non-solid tumor to the test substance, wherein an inhibitory effect of the test substance on the tumor and/or tumor cells identifies the test substance as having anti-tumor activity.

According to particular aspects, the immunodeficient mouse genetically modified to include a nucleotide sequence encoding hu-IL-15 in its genome is a genetically modified NSG, NRG, or NOG mouse, wherein the mouse expresses the hu-IL-15, is IL-2RG null such that it lacks a functional endogenous IL-2RG gene, is characterized by absence of functional endogenous mouse NK cells, wherein the mouse further includes human NK cell line cells and/or human natural killer cells wherein the human natural killer cells are produced in the mouse by differentiation of human hematopoietic stem cells in the mouse and/or by administration of PBMCs including human natural killer cells, and/or by administration of purified human NK cells, and the method includes administering human tumor cells to the immunodeficient mouse, wherein the human tumor cells form a solid or non-solid tumor in the genetically-modified, immunodeficient mouse; administering a test substance to the immunodeficient mouse; and assaying a response of the solid or non-solid tumor to the test substance, wherein an inhibitory effect of the test substance on the tumor and/or tumor cells identifies the test substance as having anti-tumor activity.

According to particular aspects, the method further includes comparing the response to a standard to determine the effect of the test substance on the human tumor cells, wherein an inhibitory effect of the test substance on the human tumor cells identifies the test substance as having anti-tumor activity.

According to particular aspects, the test substance is or includes an immunotherapeutic agent.

According to particular aspects, the test substance is or includes an immune checkpoint inhibitor.

According to particular aspects, the immune checkpoint inhibitor is or includes a PD-1 inhibitor, PD-L1 inhibitor, or CTLA-4 inhibitor.

According to particular aspects, the immune checkpoint inhibitor is or includes the immune checkpoint inhibitor is atezolizumab, avelumab, durvalumab, ipilimumab, nivolumab, or pembrolizumab, or the immune checkpoint inhibitor comprises an antigen-binding fragment of any one of the foregoing.

According to particular aspects, the test substance is or includes an antibody.

According to particular aspects, the test substance is or includes an anti-cancer agent.

An immunodeficient mouse genetically modified to include a nucleotide sequence encoding human interleukin-15 (hu-IL-15) in its genome is provided according to aspects of the present invention, wherein the mouse expresses the hu-IL-15. According to particular aspects, the immunodeficient mouse genetically modified to include a nucleotide sequence encoding human interleukin-15 (hu-IL-15) in its genome is characterized by absence of functional endogenous mouse NK cells. According to particular aspects, the immunodeficient mouse genetically modified to include a nucleotide sequence encoding human interleukin-15 (hu-IL-15) in its genome is IL-2RG null such that it lacks a functional endogenous IL-2RG gene and is characterized by absence of functional endogenous mouse NK cells. According to particular aspects, the immunodeficient mouse genetically modified to include a nucleotide sequence encoding human interleukin-15 (hu-IL-15) in its genome further includes a human xenograft including human tumor cells.

An immunodeficient NSG, NRG or NOG mouse genetically modified to include a nucleotide sequence encoding human interleukin-15 (hu-IL-15) in its genome is provided according to aspects of the present invention, wherein the NSG, NRG or NOG mouse expresses the hu-IL-15. According to particular aspects, the immunodeficient NSG, NRG or NOG mouse genetically modified to include a nucleotide sequence encoding hu-IL-15 in its genome is characterized by absence of functional endogenous mouse NK cells. According to particular aspects, the immunodeficient NSG, NRG or NOG mouse genetically modified to include a nucleotide sequence encoding human interleukin-15 (hu-IL-15) in its genome is IL-2RG null such that it lacks a functional endogenous IL-2RG gene and is characterized by absence of functional endogenous mouse NK cells. According to particular aspects, the immunodeficient NSG, NRG or NOG mouse genetically modified to include a nucleotide sequence encoding hu-IL-15 in its genome further includes a human xenograft including human tumor cells.

An immunodeficient mouse genetically modified to include a nucleotide sequence encoding hu-IL-15 in its genome is provided according to aspects of the present invention, wherein the mouse expresses the hu-IL-15 and wherein the mouse further includes human hematopoietic stem cells, human peripheral blood mononuclear cells (PBMCs), human NK cells, human NK cell line cells, or a combination of any two or more thereof. According to particular aspects, the immunodeficient mouse genetically modified to include a nucleotide sequence encoding hu-IL-15 in its genome is characterized by absence of functional endogenous mouse NK cells. According to particular aspects, the immunodeficient mouse genetically modified to include a nucleotide sequence encoding hu-IL-15 in its genome is IL-2RG null such that it lacks a functional endogenous IL-2RG gene and is characterized by absence of functional endogenous mouse NK cells. According to particular aspects, the immunodeficient mouse genetically modified to include a nucleotide sequence encoding hu-IL-15 in its genome is provided wherein the mouse expresses the hu-IL-15 and wherein the mouse includes human hematopoietic stem cells, human peripheral blood mononuclear cells (PBMCs), human NK cells, human NK cell line cells, or a combination of any two or more thereof, and further includes a human xenograft including human tumor cells.

An immunodeficient NSG, NRG or NOG mouse genetically modified to include a nucleotide sequence encoding hu-IL-15 in its genome is provided according to aspects of the present invention, wherein the NSG, NRG or NOG mouse expresses the hu-IL-15 and wherein the mouse further includes human hematopoietic stem cells, human peripheral blood mononuclear cells (PBMCs), human NK cells, human NK cell line cells, or a combination of any two or more thereof. According to particular aspects, the immunodeficient NSG, NRG or NOG mouse genetically modified to include a nucleotide sequence encoding hu-IL-15 in its genome is characterized by absence of functional endogenous mouse NK cells. According to particular aspects, the immunodeficient NSG, NRG or NOG mouse genetically modified to include a nucleotide sequence encoding hu-IL-15 in its genome is IL-2RG null such that it lacks a functional endogenous IL-2RG gene and is characterized by absence of functional endogenous mouse NK cells. According to particular aspects, the immunodeficient NSG, NRG or NOG mouse genetically modified to include a nucleotide sequence encoding hu-IL-15 in its genome expresses the hu-IL-15, wherein the mouse further includes human hematopoietic stem cells, human peripheral blood mononuclear cells (PBMCs), human NK cells, human NK cell line cells, or a combination of any two or more thereof, and wherein the mouse further includes a human xenograft including human tumor cells.

An immunodeficient mouse genetically modified to include a nucleotide sequence encoding human interleukin-15 (hu-IL-15) in its genome is provided according to aspects of the present invention, wherein the mouse expresses the hu-IL-15 and wherein the mouse further includes human NK cell line cells and/or human natural killer cells wherein the human natural killer cells are produced in the mouse by differentiation of human hematopoietic stem cells in the mouse and/or by administration of PBMCs including human natural killer cells, and/or by administration of purified human NK cells. According to particular aspects, the immunodeficient mouse genetically modified to include a nucleotide sequence encoding human interleukin-15 (hu-IL-15) in its genome is characterized by absence of functional endogenous mouse NK cells. According to particular aspects, the immunodeficient mouse genetically modified to include a nucleotide sequence encoding human interleukin-15 (hu-IL-15) in its genome is IL-2RG null such that it lacks a functional endogenous IL-2RG gene and is characterized by absence of functional endogenous mouse NK cells. According to particular aspects, the immunodeficient mouse genetically modified to include a nucleotide sequence encoding human interleukin-15 (hu-IL-15) in its genome expresses the hu-IL-15, wherein the mouse further includes human NK cell line cells and/or human natural killer cells wherein the human natural killer cells are produced in the mouse by differentiation of human hematopoietic stem cells in the mouse and/or by administration of PBMCs including human natural killer cells, and/or by administration of purified human NK cells, and wherein the mouse further includes a human xenograft including human tumor cells.

An immunodeficient NSG, NRG or NOG mouse genetically modified to include a nucleotide sequence encoding human interleukin-15 (hu-IL-15) in its genome is provided according to aspects of the present invention, wherein the NSG, NRG or NOG mouse expresses the hu-IL-15 and wherein the mouse further includes human NK cell line cells and/or human natural killer cells wherein the human natural killer cells are produced in the mouse by differentiation of human hematopoietic stem cells in the mouse and/or by administration of PBMCs including human natural killer cells, and/or by administration of purified human NK cells. According to particular aspects, the immunodeficient NSG, NRG or NOG mouse genetically modified to include a nucleotide sequence encoding human interleukin-15 (hu-IL-15) in its genome is characterized by absence of functional endogenous mouse NK cells. According to particular aspects, the immunodeficient NSG, NRG or NOG mouse genetically modified to include a nucleotide sequence encoding human interleukin-15 (hu-IL-15) in its genome is IL-2RG null such that it lacks a functional endogenous IL-2RG gene and is characterized by absence of functional endogenous mouse NK cells. According to particular aspects, the immunodeficient NSG, NRG or NOG mouse genetically modified to include a nucleotide sequence encoding human interleukin-15 (hu-IL-15) in its genome expresses the hu-IL-15, wherein the mouse further includes human NK cell line cells and/or human natural killer cells wherein the human natural killer cells are produced in the mouse by differentiation of human hematopoietic stem cells in the mouse and/or by administration of PBMCs including human natural killer cells, and/or by administration of purified human NK cells, and wherein the mouse further includes a human xenograft including human tumor cells.

A method of making a genetically-modified, immunodeficient humanized mouse model, is provided according to aspects of the present invention which includes providing an immunodeficient mouse genetically modified to include a nucleotide sequence encoding hu-IL-15 in its genome is provided according to aspects of the present invention, wherein the mouse expresses the hu-IL-15; and administering human hematopoietic stem cells, human NK cell line cells, human PBMCs, purified human NK cells or any combination of any two or more thereof to the immunodeficient mouse.

A method of making a genetically-modified, immunodeficient humanized mouse model, is provided according to aspects of the present invention which includes providing an immunodeficient mouse genetically modified to include a nucleotide sequence encoding hu-IL-15 in its genome, wherein the mouse expresses the hu-IL-15 and is characterized by absence of functional endogenous mouse NK cells; and the method includes administering hematopoietic stem cells, human NK cell line cells, human PBMCs, purified human NK cells or any combination of any two or more thereof, to the immunodeficient mouse. According to particular aspects, the immunodeficient mouse genetically modified to include a nucleotide sequence encoding human interleukin-15 (hu-IL-15) in its genome is IL-2RG null such that it lacks a functional endogenous IL-2RG gene and is characterized by absence of functional endogenous mouse NK cells; and the method includes administering hematopoietic stem cells, human NK cell line cells, human PBMCs, purified human NK cells or any combination of any two or more thereof, to the immunodeficient mouse.

A method of making a genetically-modified, immunodeficient humanized mouse model, is provided according to aspects of the present invention which includes providing an NSG, NRG, or NOG mouse genetically modified to include a nucleotide sequence encoding hu-IL-15 in its genome is provided according to aspects of the present invention, wherein the mouse expresses the hu-IL-15; and administering hematopoietic stem cells, human NK cell line cells, human PBMCs, purified human NK cells or any combination of any two or more thereof, to the genetically modified NSG, NRG, or NOG mouse. According to aspects, the immunodeficient mouse is conditioned to reduce mouse hematopoietic cells of the mouse prior to administering human hematopoietic stem cells. Conditioning the immunodeficient mouse to reduce mouse hematopoietic cells of the mouse may include irradiating the genetically-modified, immunodeficient mouse and/or administering a radiomimetic drug to the genetically-modified, immunodeficient mouse. According to aspects, no conditioning to reduce mouse hematopoietic cells of the mouse is performed prior to administering human hematopoietic stem cells. According to aspects, a method of making a genetically-modified, immunodeficient humanized mouse model further includes administering a human xenograft comprising human tumor cells to the immunodeficient mouse.

A method of making a genetically-modified, immunodeficient humanized mouse model, is provided according to aspects of the present invention which includes providing an NSG, NRG, or NOG mouse genetically modified to include a nucleotide sequence encoding hu-IL-15 in its genome, wherein the genetically modified NSG, NRG, or NOG mouse expresses the hu-IL-15 and is characterized by absence of functional endogenous mouse NK cells; and the method includes administering human hematopoietic stem cells to the genetically modified NSG, NRG, or NOG mouse. According to particular aspects, the NSG, NRG, or NOG mouse genetically modified to include a nucleotide sequence encoding human interleukin-15 (hu-IL-15) in its genome is IL-2RG null such that it lacks a functional endogenous IL-2RG gene and is characterized by absence of functional endogenous mouse NK cells; and the method includes administering hematopoietic stem cells, human NK cell line cells, human PBMCs, purified human NK cells or any combination of any two or more thereof, to the immunodeficient mouse. According to aspects, the immunodeficient mouse is conditioned to reduce mouse hematopoietic cells of the mouse prior to administering hematopoietic stem cells, human NK cell line cells, human PBMCs, purified human NK cells or any combination of any two or more thereof to the immunodeficient mouse. Conditioning the immunodeficient mouse to reduce mouse hematopoietic cells of the mouse may include irradiating the genetically-modified, immunodeficient mouse and/or administering a radiomimetic drug to the genetically-modified, immunodeficient mouse. According to aspects, no conditioning to reduce mouse hematopoietic cells of the mouse is performed prior to administering hematopoietic stem cells, human NK cell line cells, human PBMCs, purified human NK cells or any combination of any two or more thereof to the immunodeficient mouse. According to aspects, a method of making a genetically-modified, immunodeficient humanized mouse model further includes administering a human xenograft comprising human tumor cells to the immunodeficient mouse.

According to general aspects, an immunodeficient mouse is provided which is useful as a model of model system for assessment of NK-cell mediated antibody-dependent cellular toxicity (ADCC), and as a model of functions and regulation of human natural killer (NK) cells and other interleukin 15 (IL-15)-dependent cell populations and processes in studies of human immunity, cancer, infectious diseases, and other areas. According to specific aspects, an immunodeficient mouse is provided which is genetically modified to express human interleukin 15, wherein the mouse does not have or produce functional mouse natural killer cells, and wherein the mouse is modified to include human natural killer cells.

An immunodeficient mouse is provided which is useful as a model of functions and regulation of human natural killer (NK) cells and other interleukin 15 (IL-15)-dependent cell populations and processes in studies of human immunity, cancer, infectious diseases, and other areas. According to specific aspects, an immunodeficient mouse is provided which is genetically modified to express human interleukin 15, wherein the mouse does not have or produce functional mouse natural killer cells, and wherein the mouse is modified to include human natural killer cells. Methods of identifying anti-tumor activity of a test substance using a mouse of the present invention are described along with methods of making the mouse.

BRIEF DESCRIPTION OF THE DRAWINGS

In all figures herein which were analyzed for statistical significance, * signifies P<0.05,  signifies P<0.01, * signifies P<0.001, and **** signifies P<0.0001.

DETAILED DESCRIPTION OF THE INVENTION

Figure 1:
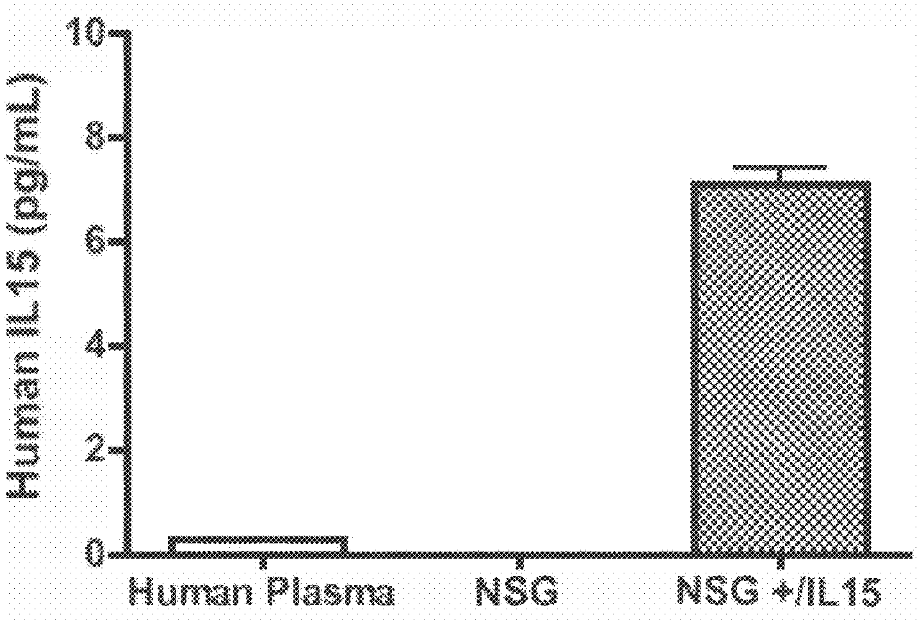
FIG. 1 is a graph showing human IL15 levels in sera from NSG-Tg(Hu-IL15) hemizygotes

Scientific and technical terms used herein are intended to have the meanings commonly understood by those of ordinary skill in the art. Such terms are found defined and used in context in various standard references illustratively including J. Sambrook and D. W. Russell, Molecular Cloning: A Laboratory Manual, Cold Spring Harbor Laboratory Press; 3rd Ed., 2001; F. M. Ausubel, Ed., Short Protocols in Molecular Biology, Current Protocols; 5th Ed., 2002; B. Alberts et al., Molecular Biology of the Cell, 4th Ed., Garland, 2002; D. L. Nelson and M. M. Cox, Lehninger Principles of Biochemistry, 4th Ed., W.H. Freeman & Company, 2004; Engelke, D. R., RNA Interference (RNAi): Nuts and Bolts of RNAi Technology, DNA Press LLC, Eagleville, PA, 2003; Herdewijn, P. (Ed.), Oligonucleotide Synthesis: Methods and Applications, Methods in Molecular Biology, Humana Press, 2004; A. Nagy, M. Gertsenstein, K. Vintersten, R. Behringer, Manipulating the Mouse Embryo: A Laboratory Manual, 3rd edition, Cold Spring Harbor Laboratory Press; Dec. 15, 2002, ISBN-10:0879695919; Kursad Turksen (Ed.), Embryonic stem cells: methods and protocols in Methods Mol Biol. 2002; 185, Humana Press; Current Protocols in Stem Cell Biology, ISBN: 9780470151808; Chu, E. and Devita, V. T., Eds., Physicians' Cancer Chemotherapy Drug Manual, Jones & Bartlett Publishers, 2005; J. M. Kirkwood et al., Eds., Current Cancer Therapeutics, 4th Ed., Current Medicine Group, 2001; Remington: The Science and Practice of Pharmacy, Lippincott Williams & Wilkins, 21st Ed., 2005; L. V. Allen, Jr. et al., Ansel's Pharmaceutical Dosage Forms and Drug Delivery Systems, 8th Ed., Philadelphia, PA: Lippincott, Williams & Wilkins, 2004; and L. Brunton et al., Goodman & Gilman's The Pharmacological Basis of Therapeutics, McGraw-Hill Professional, 12th Ed., 2011.

The singular terms "a," "an," and "the" are not intended to be limiting and include plural referents unless explicitly stated otherwise or the context clearly indicates otherwise.

The term "comprising" refers to an open group, e.g., a group comprising members A, B, and C can also include additional members. The term "consisting of" refers to a closed group, e.g., a group consisting of members A, B, and C does not include any additional members.

A mouse model of the present invention is an immunodeficient mouse genetically modified to express human IL-15 and is referred to herein as an "immunodeficient hu-IL-15 mouse." An immunodeficient hu-IL-15 mouse model described herein provides a platform for high-throughput in vivo testing of human NK cell-mediated immunotherapy by eliminating the requirement for in vitro culture of NK cells with human IL-15 and repeated in vivo injections of recombinant IL-15.

Immunodeficient Hu-IL-15 Mouse

Aspects of the present invention relate to an immunodeficient genetically modified such that the genome of the mouse includes a nucleic acid encoding human IL-15 (hu-IL-15 mouse), wherein the immunodeficient hu-IL-15 mouse expresses human IL-15 and wherein the immunodeficient hu-IL-15 mouse includes human hematopoietic stem cells. Aspects of the present invention relate to an immunodeficient hu-IL-15 mouse genetically modified such that the genome of the mouse includes a nucleic acid encoding human IL-15 (hu-IL-15 mouse), wherein the immunodeficient hu-IL-15 mouse expresses human IL-15 and wherein the immunodeficient hu-IL-15 mouse includes differentiated human hematopoietic stem cells, particularly human NK cells.

In particular aspects, a nucleotide sequence encoding human IL-15 is integrated into the genome of selected cells of the mouse. For example, the nucleotide sequence encoding human IL-15 integrated into the genome of germline cells of the mouse thereby enabling the inheritance of the nucleotide sequence encoding human IL-15 to progeny of the mouse.

Human IL-15 is identified herein as SEQ ID NO: 1 and functional variants thereof are useful in the present invention.

The term "functional variant" as used herein with reference to human IL-15 refers to a protein that retains the biological activity of human IL-15. Functional variants encompass, for example, those variants of human IL-15 of SEQ ID NO:1 that retain the ability to specifically bind to human IL-15Ra, as well as regulate activation, proliferation and development of human NK cells.

Particular aspects of the present invention relate to an immunodeficient hu-IL-15 mouse whose genome includes a nucleotide sequence encoding human IL-15 having the amino acid sequence of SEQ ID NO:1 or a functional variant thereof that has at least about 85%, 90%, 91%, 92%, 93%, 94%, 95%, 96%, 97%, 98%, 99%, 99.4%, or greater, sequence identity with the amino acid sequence set forth in SEQ ID NO:1.

According to aspects of the present invention an immunodeficient hu-IL-15 mouse expresses mRNA encoding human IL-15 having the amino acid sequence of SEQ ID NO: 1 or a functional variant thereof that has at least about 85%, 90%, 91%, 92%, 93%, 94%, 95%, 96%, 97%, 98%, 99%, 99.4%, or greater, sequence identity with the amino acid sequence set forth in SEQ ID NO:1.

According to aspects of the present invention an immunodeficient hu-IL-15 mouse expresses human protein IL-15 having the amino acid sequence of SEQ ID NO:1 or a functional variant thereof that has at least about 85%, 90%, 91%, 92%, 93%, 94%, 95%, 96%, 97%, 98%, 99%, 99.4%, or greater, sequence identity with the amino acid sequence set forth in SEQ ID NO:1.

An immunodeficient hu-IL-15 mouse according to aspects of the present invention includes in its genome a nucleic acid encoding human IL-15 operably linked to a promoter wherein the human IL-15 includes the amino acid sequence of SEQ ID NO:1, or the amino acid sequence encoded by the complement of a nucleic acid which hybridizes to SEQ ID NO:2 under highly stringent hybridization conditions. It will be appreciated by those of ordinary skill in the art that, due to the degenerate nature of the genetic code, alternate nucleic acid sequences encode human IL-15 and functional variants thereof and that such alternate nucleic acids may be used in compositions and methods described herein.

To determine the percent identity of two amino acid sequences or two nucleotide sequences, the sequences are aligned for optimal comparison purposes (e.g., gaps can be introduced in a first amino acid or nucleotide sequence for optimal alignment with a second amino acid or nucleotide sequence using the default parameters of an alignment software program). The amino acids or nucleotides at corresponding amino acid positions or nucleotide positions are then compared. When a position in the first sequence is occupied by the same amino acid or nucleotide as the corresponding position in the second sequence, then the sequences are identical at that position. The percent identity between the two sequences is a function of the number of identical positions shared by the sequences (i.e., % identity=number of identical aligned positions÷total number of aligned positions·100%). In some embodiments, the two sequences have the same length.

The determination of percent identity between two sequences can be accomplished using a mathematical algorithm. A non-limiting example of a mathematical algorithm utilized for the comparison of two sequences is the algorithm of Karlin and Altschul, 1990, PNAS USA 87:2264-68, e.g., as modified as in Karlin and Altschul, 1993, PNAS USA 90:5873-77. Such an algorithm is incorporated in the NBLAST and XBLAST programs of Altschul et al, 1990, J. Mol. Biol. 215:403. BLAST nucleotide searches can be performed with the NBLAST nucleotide program parameter set, e.g., for score=100, wordlength=12, to obtain nucleotide sequences homologous to nucleotide sequences of the present invention. BLAST protein searches can be performed with the XBLAST program parameter set, e.g., to score 50, wordlength=3, to obtain amino acid sequences homologous to a protein molecule of the present invention. To obtain gapped alignments for comparison purposes, Gapped BLAST can be utilized as described in Altschul et al, 1997, Nucleic Acids Res. 25:3389-02. Alternatively, PSI BLAST can be used to perform an iterated search that detects distant relationships between molecules (id.). When utilizing BLAST, Gapped BLAST, and PSI Blast, the default parameters of the respective programs (e.g., of XBLAST and NBLAST) are used (see, e.g., the NCBI website). Another preferred, non-limiting example of a mathematical algorithm utilized to compare sequences is the algorithm of Myers and Miller, 1988, CABIOS 4:11-17. Such an algorithm is incorporated in the ALIGN program (version 2.0) which is part of the GCG sequence alignment software package. When utilizing the ALIGN program for comparing amino acid sequences, a PAM120 weight residue table, a gap length penalty of 12, and a gap penalty of 4 is used. The Clustal suite of software programs provides an additional method for aligning sequences to determine percent sequence identity.

The percent identity between two sequences is determined using techniques similar to those described above with or without allowing gaps. In calculating percent identity, only exact matches are typically counted.

The terms "hybridization" and "hybridizes" refer to pairing and binding of complementary nucleic acids. Hybridization occurs to varying extents between two nucleic acids depending on factors such as the degree of complementarity of the nucleic acids, the melting temperature, $T_m$, of the nucleic acids and the stringency of hybridization conditions, as is well known in the art. The term "stringency of hybridization conditions" refers to conditions of temperature, ionic strength, and composition of a hybridization medium with respect to particular common additives such as formamide and Denhardt's solution. Determination of particular hybridization conditions relating to a specified nucleic acid is routine and is well known in the art, for instance, as described in J. Sambrook and D. W. Russell, Molecular Cloning: A Laboratory Manual, Cold Spring Harbor Laboratory Press; 3rd Ed., 2001; and F. M. Ausubel, Ed., Short Protocols in Molecular Biology, Current Protocols; 5th Ed., 2002. High stringency hybridization conditions are those which only allow hybridization of substantially complementary nucleic acids. Typically, nucleic acids having about 85-100% complementarity are considered highly complementary and hybridize under high stringency conditions. Intermediate stringency conditions are exemplified by conditions under which nucleic acids having intermediate complementarity, about 50-84% complementarity, as well as those having a high degree of complementarity, hybridize. In contrast, low stringency hybridization conditions are those in which nucleic acids having a low degree of complementarity hybridize.

The terms "specific hybridization" and "specifically hybridizes" refer to hybridization of a particular nucleic acid to a target nucleic acid without substantial hybridization to nucleic acids other than the target nucleic acid in a sample.

Stringency of hybridization and washing conditions depends on several factors, including the Tm of the probe and target and ionic strength of the hybridization and wash conditions, as is well-known to the skilled artisan. Hybridization and conditions to achieve a desired hybridization stringency are described, for example, in Sambrook et al., Molecular Cloning: A Laboratory Manual, Cold Spring Harbor Laboratory Press, 2001; and Ausubel, F. et al., (Eds.), Short Protocols in Molecular Biology, Wiley, 2002.

Mutations can be introduced using standard molecular biology techniques such as site-directed mutagenesis and PCR-mediated mutagenesis. One of skill in the art will recognize that one or more amino acid mutations can be introduced without altering the functional properties of human IL-15. One or more nucleotide sequences encoding human IL-15 can be altered from the genes and/or mRNA encoding human IL-15, e.g., to optimize codon usage for a particular mouse or for convenience such as to add or delete restriction sites or to modify sequences that are challenging to clone, amplify, and/or sequence.

Conservative amino acid substitutions can be made in the human IL-15 protein to produce functional human IL-15 variants. Conservative amino acid substitutions are art recognized substitutions of one amino acid for another amino acid having similar characteristics. For example, each amino acid can be described as having one or more of the following characteristics: electropositive, electronegative, aliphatic, aromatic, polar, hydrophobic, and hydrophilic. A conservative substitution is a substitution of one amino acid having a specified structural or functional characteristic for another amino acid having the same characteristic. Acidic amino acids include aspartate, glutamate; basic amino acids include histidine, lysine, arginine; aliphatic amino acids include isoleucine, leucine, and valine; aromatic amino acids include phenylalanine, tyrosine, and tryptophan; polar amino acids include aspartate, glutamate, histidine, lysine, asparagine, glutamine, arginine, serine, threonine, and tyrosine; and hydrophobic amino acids include alanine, cysteine, phenylalanine, glycine, isoleucine, leucine, methionine, proline, valine, and tryptophan; and conservative substitutions include substitutions among amino acids within each group. Amino acids can also be described in terms of steric effects or relative size, e.g., alanine, cysteine, aspartate, glycine, asparagine, proline, threonine, serine, and valine are all typically considered to be small.

The term "nucleic acid" refers to RNA or DNA molecules having more than one nucleotide in any form including single-stranded, double-stranded, oligonucleotide, or polynucleotide. The term "nucleotide sequence" refers to the ordering of nucleotides in a nucleic acid.

Nucleic acids encoding human IL-15 and variants thereof can be isolated or generated recombinantly or synthetically using well-known methodology.

An immunodeficient hu-IL-15 mouse is provided according to aspects of the present invention whose genome includes an expression cassette including a nucleotide sequence encoding human IL-15 or a functional variant thereof, wherein the mouse expresses the encoded human IL-15 or functional variant thereof.

The terms "expression construct" and "expression cassette" are used herein to refer to a double-stranded recombinant nucleotide sequence containing a desired coding sequence (e.g., a nucleotide sequence encoding human IL-15) and containing one or more regulatory elements necessary or desirable for the expression of the operably-linked coding sequence. The term "regulatory element" as used herein refers to a nucleotide sequence that controls some aspect of the expression of nucleotide sequences. Exemplary regulatory elements illustratively include an enhancer, an internal ribosome entry site (IRES), an intron, an origin of replication, a polyadenylation signal (pA), a promoter, a transcription termination sequence, and an upstream regulatory domain, which contribute to the replication, transcription, and post-transcriptional processing of a nucleotide sequence. Those of ordinary skill in the art are capable of selecting and using these and other regulatory elements in an expression construct with no more than routine experimentation. Expression constructs can be generated recombinantly or synthetically using well-known methodology.

The term "operably-linked" as used herein refers to a nucleotide sequence in a functional relationship with a second nucleotide sequence As noted above, a regulatory element included in an expression cassette can be a promoter.

The term "promoter" as used herein refers to a regulatory nucleotide sequence operably-linked to a coding nucleotide sequence to be transcribed such as a nucleotide sequence encoding a desired amino acid. A promoter is generally positioned upstream of a nucleotide sequence to be transcribed and provides a site for specific-binding by RNA polymerase and other transcription factors. Thus, in particular aspects of the present invention, a nucleotide sequence encoding human IL-15 is operably-linked to a promoter. In particular aspects of the present invention, the promoter is a constitutive promoter or an inducible promoter. In particular aspects of the present invention, the promoter provides either ubiquitous, tissue-specific, or cell-type specific expression.

Ubiquitous promoters that can be included in an expression construct include, but are not limited to, a 3-phosphoglycerate kinase (PGK-1) promoter, a beta-actin promoter, a ROSA26 promoter, a heat shock protein 70 (Hsp70) promoter, an EF-1 alpha gene encoding elongation factor 1 alpha (EF1) promoter, an eukaryotic initiation factor 4A (eIF-4A1) promoter, a chloramphenicol acetyltransferase (CAT) promoter, and a cytomegalovirus (CMV) promoter.

The promoter can be, for example, a constitutive promoter. In particular aspects of the present invention, an immunodeficient hu-IL-15 mouse includes in its genome a nucleotide sequence encoding human IL-15 that is operably-linked to a constitutive promoter. In particular aspects, the promoter is capable of driving gene expression in a host mouse (e.g., an immunodeficient mouse). For example, the promoter can be a CAG promoter. The CAG promoter includes the cytomegalovirus early enhancer element ("C"), the first exon and the first intron of the chicken beta-actin gene ("A"), and the splice acceptor of the rabbit beta-globulin gene ("G"). The CAG promoter is well known and displays robust expression in mouse cells (see, e.g., Jun-ichi et al, 1989, Gene, 79 (2): 269). The CAG promoter can be modified, for example, to remove exons. Other promoters are known to drive robust gene expression in mice including the cytomegalovirus (CMV) immediate-early promoter and the simian virus 40 (SV40) early promoter, each of which may be used in various embodiments of the invention.

These and other promoters are known in the art as exemplified in Abboud et al, 2003, J. Histochem & Cytochem., 51 (7): 941-49; Schorpp et al, 1996, Nucl. Acids Res., 24 (9): 1787-88; McBurney et al, 1994, Devel. Dynamics, 200:278-93; and Majumder et al, 1996, Blood, 87 (8): 3203-11.

In addition to a promoter, one or more enhancer sequences can be included such as, but not limited to, the cytomegalovirus (CMV) early enhancer element and the SV40 enhancer element.

In various aspects of the present invention, additional included sequences include an intron sequence such as the beta globin intron or a generic intron, a transcription termination sequence, and an mRNA polyadenylation (pA) sequence such as, but not limited to SV40-pA, beta-globin-pA, and AAT-pA.

In various aspects of the present invention, an expression construct includes sequences necessary for amplification in bacterial cells, such as a selection marker (e.g., a kanamycin or ampicillin resistance gene) and an origin of replication.

Methods for designing genes and positioning promoters in transgenic constructs are known (see, e.g., Haruyama et al, 2009, Curr. Protoc. Cell Biol., 19.10).

An immunodeficient hu-IL-15 mouse is provided according to aspects of the present invention whose genome includes an expression cassette including a nucleotide sequence encoding human IL-15 or a functional variant thereof, wherein the nucleotide sequence is operably-linked to a promoter and a polyadenylation signal, and the mouse expresses the encoded human IL-15 or functional variant thereof.

An expression construct can be introduced into fertilized mouse oocytes, a preimplantation mouse embryo or into mouse stem cells (embryonic stem cells or induced pluripotent stem cells) to generate a genetically modified mouse using well-known methods.

For methods of introduction of an expression construct into a mouse preimplantation embryo, the expression construct can be linearized before injection into the embryo.

Preferably, the expression construct is injected into fertilized oocytes. Fertilized oocytes are collected from superovulated females the day after mating (0.5 days post coitum) and injected with the expression construct. The injected oocytes are either cultured overnight or transferred directly into oviducts of 0.5-day post coitum pseudopregnant females. Methods for superovulation, harvesting of oocytes, expression construct injection, and embryo transfer are known in the art and described, for example, in Manipulating the Mouse Embryo: A Laboratory Manual, 3rd edition, Cold Spring Harbor Laboratory Press; Dec. 15, 2002, ISBN-10:0879695919. Offspring can be tested for the presence of the exogenous nucleotide sequence encoding human IL-15, or functional variant thereof, by DNA analysis, such as by PCR, Southern blot, or nucleotide sequencing. Mice that carry the exogenous nucleotide sequence can be tested for protein expression such as by ELISA or Western blot analysis.

Alternatively, an expression construct is introduced by a technique such as electroporation, calcium-phosphate precipitation, or lipofection. The cells are then screened for transgene integration by DNA analysis, such as PCR, Southern blot, or nucleotide sequencing. Cells with the correct integration can be tested for functional expression by protein analysis for human IL-15, or functional variant thereof, using for example, ELISA or Western blot analysis.

Embryonic stem cells are grown in media optimized for the particular cell line. Typically, embryonic stem cell media contains 15% fetal bovine serum (FBS) or synthetic or semi-synthetic equivalents, 2 mM glutamine, 1 mM sodium pyruvate, 0.1 mM non-essential amino acids, 50 U/mL penicillin and streptomycin, 0.1 mM 2-mercaptoethanol, and 1000 U/mL LIF (plus, for some cell lines chemical inhibitors of differentiation) in Dulbecco's Modified Eagle Media (DMEM). A detailed description is known in the art (Tremml et al, 2008, Current Protocols in Stem Cell Biology, Chapter 1:Unit 1C.4). For a review of inhibitors of embryonic stem cell differentiation, see Buehr et al, 2003, Genesis of embryonic stem cells, Philosophical Transactions of the Royal Society B: Biological Sciences 358:1397-1402.

Selected cells incorporating the expression construct can be injected into preimplantation embryos. For microinjection, embryonic stem cells or induced pluripotent stem cells are rendered to single cells using a mixture of trypsin and EDTA, followed by resuspension in embryonic stem cell media. Groups of single cells are selected using a finely drawn-out glass needle (20-25 micrometer inside diameter) and introduced through the embryo's zona pellucida and into the blastocysts cavity (blastocoel) using an inverted microscope fitted with micromanipulators. Stem cells can also be injected into early stage embryos (e.g., 2-cell, 4-cell, 8-cell, premorula, or morula). Injection may be assisted with a laser or piezo-pulsed drilled opening in the zona pellucida. Approximately 9-10 selected stem cells (embryonic stem cells or induced pluripotent stem cells) are injected per blastocyst, or 8-cell stage embryo, 6-9 stem cells per 4-cell stage embryo, and about 6 stem cells per 2-cell stage embryo. Following stem cell introduction, embryos are allowed to recover for a few hours at 37° C. in 5% $CO_2$, 5% O2 in nitrogen or cultured overnight before transfer into pseudopregnant recipient females. In a further alternative to stem cell injection, stem cells can be aggregated with morula stage embryos. All of these methods are well established and can be used to produce stem cell chimeras. For a more detailed description, see, e.g., Manipulating the Mouse Embryo: A Laboratory Manual, 3rd edition (Nagy, Gertsenstein, Vintersten, and Behringer, Cold Spring Harbor Laboratory Press, Dec. 15, 2002, ISBN-10:0879695919; see also Nagy et al, 1990, Development 110:815-821; Kraus et al, 2010, Genesis 48:394-399; and U.S. Pat. Nos. 7,576,259, 7,659,442, and 7,294,754).

Pseudopregnant embryo recipients are prepared using methods known in the art. Briefly, fertile female mice at 6-8 weeks of age are mated with vasectomized or sterile males to induce a hormonal state conducive to supporting surgically introduced embryos. At 2.5 days post coitum (dpc) up to 15 of the stem cell containing blastocysts are introduced into the uterine horn very near to the uterus-oviduct junction. For early stage embryos and morula, such embryos are either cultured in vitro into blastocysts or implanted into the oviducts of 0.5 dpc or 1.5 dpc pseudopregnant females according to the embryo stage. Chimeric pups from the implanted embryos are born 16-20 days after the transfer depending on the embryo age at implantation. Chimeric males are selected for breeding. Offspring can be analyzed for transmission of the embryonic stem cell genome, for example, by coat color and/or genetic analysis, such as PCR, Southern blot, or nucleotide sequencing. Protein expression (e.g., of human IL-15 or a functional variant thereof) can be analyzed by protein analysis (Western blot, ELISA) or other functional assays. Offspring expressing the nucleotide sequence encoding hu-IL-15, or functional variant thereof, can be intercrossed to create mice homozygous for the transgene. The transgenic mice can be crossed with immunodeficient mice to create a congenic immunodeficient strain expressing hu-IL-15, or functional variant thereof.

A nucleotide sequence encoding hu-IL-15, or functional variant thereof, can also be targeted into a specific locus of the stem cell genome that is known to result in reliable expression such as the Hprt or the Rosa26 locus. For targeted transgenics, a targeting construct can be made using recombinant DNA techniques. The targeting construct can optionally include 5' and 3' sequences that are homologous to the endogenous gene target. The targeting construct can optionally further include a selectable marker such as neomycin phosphotransferase, hygromycin, or puromycin, a nucleic acid encoding human IL-15, and a polyadenylation signal, for example. To ensure correct transcription and translation of a nucleotide sequence encoding a gene, for example, the sequence is either in frame with the endogenous gene locus, or a splice acceptor site and internal ribosome entry site (IRES) sequence are included. Such a targeting construct can be transfected into stem cells, and the stem cells can be screened to detect the homologous recombination event using PCR, Southern blot, or nucleotide sequencing. Cells with the correct homologous recombination event can be further analyzed for transgene expression by protein analysis, such as by ELISA or Western blot analysis. If desired, the selectable marker can be removed, for example, by treating the stem cells with Cre recombinase. After Cre recombinase treatment, the cells are analyzed for the presence of the nucleotide sequence encoding the gene. Cells with the correct genomic event can be selected and injected into preimplantation embryos as described above. Chimeric males are selected for breeding. Offspring can be analyzed for transmission of the embryonic stem cell genome by coat color and genetic analysis, such as PCR, Southern blot, or nucleotide sequencing, and they can be tested for protein expression such as by protein analysis (Western blot, ELISA) or other functional assays. Offspring expressing the desired IL-15 or functional IL-15 variant protein can be intercrossed to create mice homozygous for the transgene. Transgenic mice can be crossed with immunodeficient mice to create a congenic immunodeficient strain with the transgene.

Particular embodiments of the present invention provide transgenic mice that include a nucleotide sequence encoding human IL-15, or functional variant thereof, in substantially all of their cells, as well as transgenic mice that include a nucleotide sequence encoding human IL-15, or functional variant thereof, in some, but not all of their cells. In particular aspects of the present invention, one or multiple copies (such as concatamers) of the nucleotide sequence encoding human IL-15, or functional variant thereof, can be integrated into the genomes of the cells of the transgenic mice.

Any of various methods can be used to introduce a nucleotide sequence encoding human IL-15, or functional variant thereof, into mice to produce transgenic #14530752v1-26-mice expressing human IL-15, or functional variant thereof. Such techniques are well-known in the art and include, but are not limited to, pronuclear microinjection and transformation of embryonic stem cells. Methods for generating transgenic mice that can be used include, but are not limited to, those described in Sundberg and Ichiki, (Eds.), Genetically Engineered Mice Handbook, CRC Press, 2006; Hofker and van Deursen, (Eds.), Transgenic Mouse Methods and Protocols, Humana Press, 2002; Joyner, Gene Targeting: A Practical Approach, Oxford University Press, 2000; Manipulating the Mouse Embryo: A Laboratory Manual, 3rd edition, Cold Spring Harbor Laboratory Press, Dec. 15, 2002, ISBN-10:0879695919; Turksen (Ed.), Embryonic stem cells: methods and protocols in Methods Mol Biol. 2002, 185, Humana Press; Current Protocols in Stem Cell Biology, ISBN: 978047015180; Meyer et al, PNAS USA, 107 (34):15022-26.

Homology-based recombination gene modification strategies can be used to genetically modify an immunodeficient mouse by "knock-in" to introduce a nucleotide sequence encoding human IL-15, or functional variant thereof, into the genome of the immunodeficient mouse, such as homing endonucleases, integrases, meganucleases, transposons, nuclease-mediated processes using a zinc finger nuclease (ZFN), a Transcription Activator-Like (TAL), a Clustered Regularly Interspaced Short Palindromic Repeats (CRISPR)-Cas, or a *Drosophila* Recombination-Associated Protein (DRAP) approach. See, for example, Cerbini et al., PLOS One. 2015; 10(1): e0116032; Shen et al., PLOS ONE 8(10): e77696; and Wang et al., Protein & Cell, February 2016, Volume 7, Issue 2, pp 152-156.

Immunodeficiency

The term "immunodeficient mouse" refers to a mouse characterized by one or more of: a lack of functional immune cells, such as T cells and B cells; a DNA repair defect; a defect in the rearrangement of genes encoding antigen-specific receptors on lymphocytes; and a lack of immune functional molecules such as IgM, IgG1, IgG2a, IgG2b, IgG3 and IgA. Immunodeficient mice can be characterized by one or more deficiencies in a gene involved in immune function, such as Rag1 and Rag2 (Oettinger, M. A et al., Science, 248:1517-1523, 1990; and Schatz, D. G. et al., Cell, 59:1035-1048, 1989) Immunodeficient mice may have any of these or other defects which result in abnormal immune function in the mice.

According to particular aspects, an immunodeficient hu-IL-15 mouse has a defect in its endogenous gene encoding interleukin-2 receptor γ subunit (IL-2RG) which causes the mouse to express a defective endogenous interleukin-2 receptor γ subunit and/or a reduced amount of endogenous interleukin-2 receptor γ subunit, or the mouse may not express an endogenous interleukin-2 receptor γ subunit at all. A major consequence of Il2rg deficiency is an absence of functional endogenous mouse NK cells. Thus, according to particular aspects of the present invention, an immunodeficient hu-IL-15 mouse has an Il2rg deficiency such that the mouse has an absence of functional endogenous mouse NK cells. According to particular further aspects an immunodeficient hu-IL-15 mouse of the present invention is IL-2RG null such that it lacks a functional endogenous IL-2RG gene and lacks functional endogenous mouse NK cells.

In further aspects, an immunodeficient hu-IL-15 mouse has a defect in its endogenous gene encoding DNA-dependent protein kinase, catalytic subunit (Prkdc) which causes the mouse to express a defective endogenous DNA-dependent protein kinase, catalytic subunit and/or a reduced amount of endogenous DNA-dependent protein kinase, catalytic subunit, or the mouse may not express endogenous DNA-dependent protein kinase, catalytic subunit at all. An immunodeficient hu-IL-15 mouse of the present invention can optionally be Prkdc null such that it lacks a functional endogenous Prkdc gene.

"Endogenous," as used herein in relation to genes and the proteins they encode, refers to genes present in the genome of the mouse at their native gene locus.

In various aspects of the present invention, an immunodeficient hu-IL-15 mouse is IL-2RG null and/or Prkdc null, lacking functional endogenous IL-2RG and Prkdc genes. An immunodeficient hu-IL-15 mouse of the present invention can optionally include a Prkdc knockout and/or an IL-2rg knockout. In various aspects of the present invention, the immunodeficient hu-IL-15 mouse does not express IL-2rg, does not express Prkdc, or does not express either IL-2rg and Prkdc.

In various aspects of the present invention, an immunodeficient hu-IL-15 mouse has severe-combined immunodeficiency. The term "severe combined immune deficiency" or "SCID" refers to a condition characterized by the absence of T cells and a lack of B cell function.

Common forms of SCID include: X-linked SCID, which is characterized by gamma chain gene mutations in the IL-2RG gene and the lymphocyte phenotype T(−) B(+) NK(−). and autosomal recessive SCID. Autosomal recessive SCID can be characterized by Jak3 gene mutations and the lymphocyte phenotype T(−) B(+) NK(−), ADA gene mutations and the lymphocyte phenotype T(−) B(−) NK(−), IL-7R alpha-chain mutations and the lymphocyte phenotype T(−) B(+) NK(+), CD3 delta or epsilon mutations and the lymphocyte phenotype T(−) B(+) NK(+), RAG1/RAG2 mutations and the lymphocyte phenotype T(−) B(−) NK(+), Artemis gene mutations and the lymphocyte phenotype T(−) B(−) NK(+), and CD45 gene mutations and the lymphocyte phenotype T(−) B(+) NK(+).

According to aspects of the present invention, an immunodeficient hu-IL-15 mouse has the severe combined immunodeficiency mutation ($Prkde^{scid}$), commonly referred to as the scid mutation. The scid mutation is well-known and located on mouse chromosome 16 as described in Bosma et al, 1989, Immunogenetics 29:54-56. Mice homozygous for the scid mutation are characterized by an absence of functional T cells and B cells, lymphopenia, hypoglobulinemia, and a normal hematopoetic microenvironment. The scid mutation can be detected, for example, by the detection of markers for the scid mutation using well-known methods such as PCR or flow cytometry.

An immunodeficient hu-IL-15 mouse according to aspects of the present invention has an IL2 receptor gamma chain deficiency. The term "IL2 receptor gamma chain deficiency" refers to decreased IL2 receptor gamma chain. Decreased IL2 receptor gamma chain can be due to gene deletion or mutation. Decreased IL2 receptor gamma chain can be detected, for example, by detection of IL2 receptor gamma chain gene deletion or mutation and/or detection of decreased IL2 receptor gamma chain expression using well-known methods.

An immunodeficient hu-IL-15 mouse according to aspects of the present invention has severe combined immunodeficiency or an IL2 receptor gamma chain deficiency in combination with severe combined immunodeficiency, wherein the #14530752v1-29-genome of the mice includes a nucleotide sequence encoding human IL-15 or a functional variant thereof.

An immunodeficient hu-IL-15 mouse according to aspects of the present invention has the scid mutation or an IL2 receptor gamma chain deficiency in combination with the scid mutation, wherein the genome of the mice includes a nucleotide sequence encoding human IL-15 or a functional variant thereof.

In various aspects of the present invention, the immunodeficient hu-IL-15 mouse is a genetically modified NSG mouse, a genetically modified NRG mouse or a genetically modified NOG mouse, wherein the genome of the genetically-modified NSG, NRG or NOG mouse includes a nucleotide sequence encoding human IL-15 or a functional variant thereof.

The terms "NOD scid gamma," "NOD-scid $IL2Rg^{null}$" and "NSG" are used interchangeably herein to refer to a well-known immunodeficient mouse strain NOD.Cg-$Prkdc^{scid}$ IL-$2rg^{tmlWjl}$/SzJ, described in detail in Shultz L D et al, 2005, J. Immunol, 174:6477-89. NSG mice combine multiple immune deficits from the NOD/ShiLtJ background, the severe combined immune deficiency (scid) mutation, and a complete knockout of the interleukin-2 receptor gamma chain. As a result, NSG mice lack mature mouse T, B, and NK cells, and they are deficient in mouse cytokine signaling pathways. NSG mice are characterized by a lack of mouse IL-2R-γ (gamma c) expression, no detectable mouse serum immunoglobulin, no mouse hemolytic complement, no mature mouse T lymphocytes, and no mature mouse natural killer cells.

An NSG mouse that expresses human IL-15, or a functional variant thereof, is referred to alternatively as a "NSG-hu-IL-15" mouse or an "NSG-Tg(Hu-IL15)" mouse, which indicates that the genome of the genetically-modified NSG mouse includes a nucleotide sequence encoding human IL-15, or a functional variant thereof, on the NOD.Cg-$Prkdc^{scid}$ IL-$2rg^{tm/Wjl}$/SzJ background, and the mouse expresses human IL-15, or a functional variant thereof.

NRG mice are well-known as NOD.Cg-$Rag1^{tmlMom}$ $Il2rg^{tm1\,Wjl}$/SzJ, described in detail in Shultz L D et al, 2008 Clin Exp Immunol 154 (2): 270-84. An NRG mouse that expresses human IL-15, or a functional variant thereof, is referred to as a "NRG-hu-IL-15" mouse, which indicates that the genome of the genetically-modified NRG mouse includes a nucleotide sequence encoding human IL-15, or a functional variant thereof, on the NOD.Cg-$Rag1^{tm1Mom}$ $Il2rg^{tm1\,Wjl}$/SzJ background, and the mouse expresses human IL-15, or a functional variant thereof. NRG mice are characterized by a lack of mouse natural killer (NK) cells.

NOG mice are well-known as NOD.Cg-$Prkde^{scid}$ $Il2rg^{tm1Sug}$/JicTac, described in detail in Ito, M. et al., Blood 100, 3175-3182 (2002). A NOG mouse that expresses human IL-15, or a functional variant thereof, is referred to as a "NOG-hu-IL-15" mouse, which indicates that the genome of the genetically-modified NOG mouse includes a nucleotide sequence encoding human IL-15, or a functional variant thereof, mouse on the NOD.Cg-$Prkde^{scid}$ $112rg^{tm1Sug}$/JicTac background, and the mouse expresses human IL-15, or a functional variant thereof. NOG mice are characterized by a lack of mouse natural killer (NK) cells.

Xenografts

Xenogeneic cells which differentiate into xenogeneic NK cells, a population of cells including xenogeneic NK cells, or a purified population of xenogeneic NK cells are administered to an immunodeficient hu-IL-15 mouse, producing an immunodeficient hu-IL-15 mouse having natural killer cells produced in the mouse by differentiation of the xenogeneic cells in the mouse. Xenogeneic cells which differentiate into NK cells in a mouse include xenogeneic hematopoietic stem cells. Xenogeneic peripheral blood mononuclear cells (PBMC) are a population of cells including xenogeneic NK cells.

Hematopoietic Stem Cell Xenografts

Various aspects of the invention relate to administering xenogeneic hematopoietic stem cells (HSC) to an immunodeficient hu-IL-15 mouse, producing an immunodeficient hu-IL-15 mouse having engrafted HSC.

The xenogeneic HSC are human HSC according to aspects of the present invention.

The term "xenogeneic HSC" as used herein refers to multipotent stem cells expressing c-Kit receptor. Examples of multipotent stem cells expressing c-Kit receptor include, but are not limited to, haematopoietic stem cells, also known as hemocytoblasts. C-Kit receptor is well-known in the art, for example as described in Vandenbark G R et al., 1992, Cloning and structural analysis of the human c-kit gene, Oncogene 7(7): 1259-66; and Edling C E, Hallberg B, 2007, c-Kit--a hematopoietic cell essential receptor tyrosine kinase, Int. J. Biochem. Cell Biol. 39(11):1995-8.

Isolation of xenogeneic HSC, administration of the xenogeneic HSC to a host mouse and methods for assessing engraftment in the host mouse thereof are well-known in the art.

Hematopoietic stem cells for administration to an immunodeficient hu-IL-15 mouse can be obtained from any tissue containing HSC such as, but not limited to, umbilical cord blood, bone marrow, GM-CSF-mobilized peripheral blood and fetal liver.

Xenogeneic HSC can be administered into newborn mice by administration via various routes, such as, but not limited to, into the heart, liver and/or facial vein. Xenogeneic HSC can be administered into adult mice by various routes, such as, but not limited to, administration into the tail vein, into the femur bone marrow cavity or into the spleen. In a further example, fetal liver containing the xenogeneic HSC can be engrafted under the renal capsule.

Administering xenogeneic HSC to an immunodeficient hu-IL-15 mouse can include administering a composition comprising xenogeneic HSC to the immunodeficient hu-IL-15 mouse. The composition can further include, for example, water, a tonicity-adjusting agent (e.g., a salt such as sodium chloride), a pH buffer (e.g., citrate), and/or a sugar (e.g., glucose).

Engraftment of xenogeneic hematopoietic stem cells in an immunodeficient hu-IL-15 mouse is characterized by the presence of differentiated xenogeneic hematopoietic cells in the immunodeficient hu-IL-15 mouse. Engraftment of xenogeneic HSC can be assessed by any of various methods, such as, but not limited to, flow cytometric analysis of cells in the animals to which the xenogeneic HSC are administered at one or more time points following the administration of HSC.

Exemplary methods for isolation of xenogeneic HSC, administration of the xenogeneic HSC to a host mouse and methods for assessing engraftment thereof are described herein and in T. Pearson et al., Curr. Protoc. Immunol. 81:15.21.1-15.21.21, 2008; Ito, M. et al, Blood 100:3175-3182; Traggiai, E. et al, Science 304:104-107; Ishikawa, F. et al, Blood 106:1565-1573; Shultz, L. D. et al, J. Immunol. 174:6477-6489; Holyoake T L et al, Exp Hematol., 1999, 27 (9): 1418-27.

According to aspects of the present invention, the xenogeneic HSC administered to an immunodeficient hu-IL-15 mouse are isolated from an original source material to obtain a population of cells enriched in HSCs. The isolated xenogeneic HSCs may or may not be pure. According to aspects, xenogeneic HSCs are purified by selection for a cell marker, such as CD34. According to aspects, administered xenogeneic HSCs are a population of cells in which CD34+ cells constitute about 1-100% of total cells, although a population of cells in which CD34+ cells constitute fewer than 1% of total cells can be used. According to embodiments, administered xenogeneic HSCs are T cell depleted cord blood cells in which CD34+ cells make up about 1-3% of total cells, lineage depleted cord blood cells in which CD34+ cells make up about 50% of total cells, or CD34+ positively selected cells in which CD34+ cells make up about 90% of total cells.

The number of xenogeneic HSCs administered is not considered limiting with regard to generation of a xenogeneic hematopoietic and immune system in an immunodeficient hu-IL-15 mouse. A single xenogeneic HSC can generate a hematopoietic and immune system in a host immunodeficient hu-IL-15 mouse. Thus, the number of administered xenogeneic HSCs is generally in the range of $1\times10^3$ to $1\times10^6$ (1,000 to 1,000,000) CD34+ cells where the recipient is a mouse, although more or fewer can be used.

Thus, a method according to aspects of the present invention can include administering about $10^3$ (1000) to about $10^6$ (1,000,000), about $10^3$ to about $10^5$, about $10^4$ to about $10^6$, about $10^5$ to about $10^7$, about $1\times10^3$ to about $1\times10^4$, about $5\times10^3$ to about $5\times10^4$, about $1\times10^4$ to about $1\times10^5$, about $5\times10^4$ to about $5\times10^5$, about $1\times10^5$ to about $1\times10^6$, about $5\times10^5$ to about $5\times10^6$, about $1\times10^6$ to about $1\times10^7$, about $2\times10^4$ to about $5\times10^5$, or about $5\times10^4$ to about $2\times10^5$ xenogeneic HSC, such as human hematopoietic stem cells, to the immunodeficient hu-IL-15 mouse. The method can include administering at least about $1\times10^2$, about $2\times10^2$, about $3\times10^2$, about $4\times10^2$, about $5\times10^2$, about $6\times10^2$, about $7\times10^2$, about $8\times10^2$, about $9\times10^2$, about $1\times10^3$, about $2\times10^3$, about $3\times10^3$, about $4\times10^3$, about $5\times10^3$, about $6\times10^3$, about $7\times10^3$, about $8\times10^3$, about $9\times10^3$, about $1\times10^4$, about $2\times10^4$, about $3\times10^4$, about $4\times10^4$, about $5\times10^4$, about $6\times10^4$, about $7\times10^4$, about $8\times10^4$, about $9\times10^4$, about $1\times10^5$, about $2\times10^5$, about $3\times10^5$, about $4\times10^5$, about $5\times10^5$, about $6\times10^5$, about $7\times10^5$, about $8\times10^5$, about $9\times10^5$, about $1\times10^6$, about $2\times10^6$, about $3\times10^6$, about $4\times10^6$, about $5\times10^6$, about $6\times10^6$, about $7\times10^6$, about $8\times10^6$, about $9\times10^6$, or about $1\times10^7$ xenogeneic HSC, such as human hematopoietic stem cells, to the immunodeficient hu-IL-15 mouse. The method can include administering about $1\times10^2$, about $2\times10^2$, about $3\times10^2$, about $4\times10^2$, about $5\times10^2$, about $6\times10^2$, about $7\times10^2$, about $8\times10^2$, about $9\times10^2$, about $1\times10^3$, about $2\times10^3$, about $3\times10^3$, about $4\times10^3$, about $5\times10^3$, about $6\times10^3$, about $7\times10^3$, about $8\times10^3$, about $9\times10^3$, about $1\times10^4$, about $2\times10^4$, about $3\times10^4$, about $4\times10^4$, about $5\times10^4$, about $6\times10^4$, about $7\times10^4$, about $8\times10^4$, about $9\times10^4$, about $1\times10^5$, about $2\times10^5$, about $3\times10^5$, about $4\times10^5$, about $5\times10^5$, about $6\times10^5$, about $7\times10^5$, about $8\times10^5$, about $9\times10^5$, about $1\times10^6$, about $2\times10^6$, about $3\times10^6$, about $4\times10^6$, about $5\times10^6$, about $6\times10^6$, about $7\times10^6$, about $8\times10^6$, about $9\times10^6$, or about $1\times10^7$ xenogeneic HSC, such as human HSC, to the immunodeficient hu-IL-15 mouse. Those of ordinary skill will be able to determine a number of xenogeneic HSC that should be administered to a specific mouse using no more than routine experimentation.

Engraftment is successful where xenogenic HSCs and/or cells differentiated from the xenogeneic HSCs in the recipient immunodeficient hu-IL-15 mouse are detected at a time when the majority of any administered non-HSC have degenerated. Detection of differentiated xenogeneic HSC cells can be achieved by detection of xenogeneic DNA in the recipient immunodeficient hu-IL-15 mouse or detection of intact xenogeneic HSCs and cells differentiated from the xenogeneic HSCs, for example. Serial transfer of CD34+ cells into a secondary recipient and engraftment of a xenogeneic hematopoietic system is a further test of HSC engraftment in the primary recipient. Engraftment can be detected by flow cytometry as 0.05% or greater xenogeneic CD45+ cells in the blood, spleen or bone marrow of the recipient immunodeficient hu-IL-15 mouse at 10-12 weeks after administration of the xenogeneic HSC.

Engraftment of xenogeneic haematopoietic stem cells (HSC) in an immunodeficient hu-IL-15 mouse according to aspects of the present invention includes "conditioning" of the immunodeficient hu-IL-15 mouse prior to administration of the xenogeneic HSC, for example by sub-lethal irradiation of the recipient animal with high frequency electromagnetic radiation, generally using gamma radiation, or treatment with a radiomimetic drug such as busulfan or nitrogen mustard. Conditioning is believed to reduce numbers of host hematopoietic cells, create appropriate microenvironmental factors for engraftment of xenogeneic HSC, and/or create microenvironmental niches for engraftment of xenogeneic HSC. Standard methods for conditioning are known in the art, such as described herein and in J. Hayakawa et al, 2009, Stem Cells, 27 (1): 175-182.

Methods are provided according to aspects of the present invention which include administration of xenogeneic HSC to an immunodeficient hu-IL-15 mouse without "conditioning" the immunodeficient hu-IL-15 mouse prior to administration of the xenogeneic HSC. Methods are provided according to aspects of the present invention which include administration of xenogeneic HSC to an immunodeficient hu-IL-15 mouse without "conditioning" by radiation or radiomimetic drugs of the immunodeficient hu-IL-15 mouse prior to administration of the xenogeneic HSC.

Various aspects of the invention relate to administering xenogeneic hematopoietic stem cells (HSC) to an immunodeficient hu-IL-15 mouse, producing an immunodeficient hu-IL-15 mouse having engrafted HSC. The engrafted xenogeneic HSC differentiate to produce an immunodeficient hu-IL-15 mouse with a xenogeneic immune system or components thereof.

Administration of xenogeneic HSC to an immunodeficient hu-IL-15 mouse results in the production of differentiated xenogeneic cells of hematopoietic lineage in the mouse. For example, administration of xenogeneic HSC to an immunodeficient hu-IL-15 mouse results in the production of xenogeneic myeloid-lineage and xenogeneic lymphoid-lineage cells by the mouse such as xenogeneic CD33+ myeloid cells, xenogeneic myeloid progenitor cells, xenogeneic mast cells, xenogeneic myeloid dendritic cells, xenogeneic B cells, xenogeneic T cells, xenogeneic T helper cells, xenogeneic cytotoxic T cells, and/or xenogeneic Treg cells. According to aspects of the present invention, human HSC are administered to an immunodeficient hu-IL-15 mouse which differentiate such that the mouse includes one or more of: human $CD33^+$ myeloid cells, human myeloid progenitor cells, human mast cells, human myeloid dendritic cells, human B cells, human T cells, human T helper cells, human cytotoxic T cells, and/or human Treg cells.

Administration of xenogeneic HSC to an immunodeficient hu-IL-15 mouse results in the production of differentiated xenogeneic cells of hematopoietic lineage that can be characterized by flow cytometry. For example, administration of human HSC to an immunodeficient hu-IL-15 mouse results in the production of differentiated human cells of hematopoietic lineage that can be characterized by flow cytometry, including human leukocytes selected from 1, 2, 3, 4, 5, 6, 7, 8, 9, 10, or all of $CD45^+$, $CD20^+$, $CD20^+CD45^+$, $CD3^+$, $CD3^+CD45^+$, $CD33^+$, $CD33^+CD45^+$, $CD14^+$, $CD14^+CD45^+$, $CD56^+$, and $CD56^+CD45^+$ human leukocytes.

Administration of human HSC to an immunodeficient hu-IL-15 mouse results in the production of differentiated human cells of hematopoietic lineage, including human NK cells.

Peripheral Blood Mononuclear Cell Xenografts

Various aspects of the invention relate to administering xenogeneic peripheral blood mononuclear cells (PBMC) to an immunodeficient hu-IL-15 mouse, producing an immunodeficient hu-IL-15 mouse having xenogeneic NK cells.

The xenogeneic PBMC are human PBMC according to aspects of the present invention.

The term "xenogeneic PBMC" as used herein refers to a population of cells obtained from peripheral blood that naturally includes NK cells, typically in a range from 1-10%, but can be higher or lower.

Isolation of xenogeneic PBMC and administration of the xenogeneic PBMC to a host mouse are well-known in the art.

Xenogeneic PBMC for administration to an immunodeficient hu-IL-15 mouse can be obtained from peripheral blood.

Xenogeneic PBMC can be administered into newborn mice by administration via various routes, such as, but not limited to, into the heart, liver and/or facial vein. Xenogeneic PBMC can be administered into adult mice by various routes, such as, but not limited to, administration into the tail vein, into the femur bone marrow cavity or into the spleen. In a further example, fetal liver containing the xenogeneic PBMC can be engrafted under the renal capsule.

Administering xenogeneic PBMC to an immunodeficient hu-IL-15 mouse can include administering a composition comprising xenogeneic PBMC to the immunodeficient hu-IL-15 mouse. The composition can further include, for example, water, a tonicity-adjusting agent (e.g., a salt such as sodium chloride), a pH buffer (e.g., citrate), and/or a sugar (e.g., glucose).

Engraftment of xenogeneic PBMC in an immunodeficient hu-IL-15 mouse is characterized by the presence of xenogeneic natural killer cells in the immunodeficient hu-IL-15 mouse. Presence of xenogeneic natural killer cells can be assessed by any of various methods, such as, but not limited to, flow cytometric analysis of cells in the animals to which the xenogeneic PBMC are administered at one or more time points following the administration of PBMC.

According to aspects of the present invention, the xenogeneic PBMC administered to an immunodeficient hu-IL-15 mouse are isolated from an original source material to obtain a population of cells enriched in PBMCs and/or NK cells. The isolated xenogeneic PBMCs and/or NK cells may or may not be pure. According to aspects, xenogeneic PBMCs and/or NK cells are purified by selection for a cell marker, such as CD16 or CD56. According to aspects, administered xenogeneic PBMCs are a population of cells in which CD16+ and/or CD56+ cells constitute about 1-100% of total cells, although a population of cells in which CD16+ and/or CD56 cells constitute fewer than 1% of total cells can be used. According to embodiments, administered xenogeneic PBMCs are T cell depleted cells in which CD16+ and/or CD56+ cells make up about 1-3% of total cells or positively selected cells in which CD16+ and/or CD56+ cells make up about 90% of total cells.

The number of xenogeneic PBMCs administered is not considered limiting with regard to generation of a model of NK cells in an immunodeficient hu-IL-15 mouse. Thus, the number of administered xenogeneic PBMCs is generally in the range of $1\times10^5$ to $1\times10^8$ (100,000 to 100,000,000) PBMCs where the recipient is a mouse, although more or fewer can be used.

Thus, a method according to aspects of the present invention can include administering about $1\times10^5$ to $1\times10^8$ (100,000 to 100,000,000) PBMCs, $10^5$ (100,000) to about $10^7$ (10,000,000), about $1\times10^5$ to about $1\times10^6$, about $5\times10^5$ to about $5\times10^6$, or about $1\times10^6$ to about $1\times10^7$, xenogeneic PBMCs, such as human PBMCs, to the immunodeficient hu-IL-15 mouse. The method can include administering at least about $1\times10^5$, about $2\times10^5$, about $3\times10^5$, about $4\times10^5$, about $5\times10^5$, about $6\times10^5$, about $7\times10^5$, about $8\times10^5$, about $9\times10^5$, about $1\times10^6$, about $2\times10^6$, about $3\times10^6$, about $4\times10^6$, about $5\times10^6$, about $6\times10^6$, about $7\times10^6$, about $8\times10^6$, about $9\times10^6$, about $1\times10^7$, about $2\times10^7$, about $3\times10^7$, about $4\times10^7$, about $5\times10^7$, about $6\times10^7$, about $7\times10^7$, about $8\times10^7$, about $9\times10^7$, or about $1\times10^8$, xenogeneic PBMCs, such as human PBMCs, to the immunodeficient hu-IL-15 mouse. Those of ordinary skill will be able to determine a number of xenogeneic PBMCs that should be administered to a specific mouse using no more than routine experimentation.

Engraftment is successful where xenogenic NK cells in the recipient immunodeficient hu-IL-15 mouse are detected at a time when the majority of any administered non-PBMCs have degenerated. Engraftment can be detected by flow cytometry as 0.05% or greater xenogeneic CD16+ and/or CD56+ cells in the blood or spleen of the recipient immunodeficient hu-IL-15 mouse at 10-12 weeks after administration of the xenogeneic PBMCs.

Engraftment of xenogeneic PBMCs in an immunodeficient hu-IL-15 mouse according to aspects of the present invention includes "conditioning" of the immunodeficient hu-IL-15 mouse prior to administration of the xenogeneic PBMCs, for example by sub-lethal irradiation of the recipient animal with high frequency electromagnetic radiation, generally using gamma radiation, or treatment with a radiomimetic drug such as busulfan or nitrogen mustard. Conditioning is believed to reduce numbers of host hematopoietic cells, create appropriate microenvironmental factors for maintenance and/or production of NK cells, and/or create microenvironmental niches for maintenance and/or production of NK cells. Standard methods for conditioning are known in the art, such as described herein and in J. Hayakawa et al, 2009, Stem Cells, 27(1):175-182.

Methods are provided according to aspects of the present invention which include administration of xenogeneic PBMCs to an immunodeficient hu-IL-15 mouse without "conditioning" the immunodeficient hu-IL-15 mouse prior to administration of the xenogeneic PBMCs. Methods are provided according to aspects of the present invention which include administration of xenogeneic PBMCs to an immunodeficient hu-IL-15 mouse without "conditioning" by radiation or radiomimetic drugs of the immunodeficient hu-IL-15 mouse prior to administration of the xenogeneic PBMCs.

Various aspects of the invention relate to administering xenogeneic PBMCs to an immunodeficient hu-IL-15 mouse, producing an immunodeficient hu-IL-15 mouse having xenogeneic NK cells.

Administration of xenogeneic PBMCs to an immunodeficient hu-IL-15 mouse results in the maintenance and/or production of xenogeneic natural killer cells in the mouse.

Administration of xenogeneic PBMCs to an immunodeficient hu-IL-15 mouse results in the maintenance and/or production of xenogeneic PBMCs in the mouse that can be characterized by flow cytometry. For example, administration of human PBMCs to an immunodeficient hu-IL-15 mouse results in the maintenance and/or production of natural killer cells in the mouse that can be characterized by flow cytometry, including human CD16+ and/or CD56+ human NK cells.

NK Cell Xenografts

Various aspects of the invention relate to administering purified xenogeneic natural killer cells (NK cells) to an immunodeficient hu-IL-15 mouse, producing an immunodeficient hu-IL-15 mouse having xenogeneic NK cells.

The xenogeneic NK cells are human NK cells according to aspects of the present invention.

Purification of xenogeneic NK cells and administration of the xenogeneic NK cells to a host mouse are well-known in the art.

Xenogeneic NK cells for administration to an immunodeficient hu-IL-15 mouse can be obtained from peripheral blood.

Xenogeneic NK cells can be administered into newborn mice by administration via various routes, such as, but not limited to, into the heart, liver and/or facial vein. Xenogeneic NK cells can be administered into adult mice by various routes, such as, but not limited to, administration into the tail vein, into the femur bone marrow cavity or into the spleen. In a further example, fetal liver containing the xenogeneic NK cells can be engrafted under the renal capsule.

Administering xenogeneic NK cells to an immunodeficient hu-IL-15 mouse can include administering a composition comprising xenogeneic NK cells to the immunodeficient hu-IL-15 mouse. The composition can further include, for example, water, a tonicity-adjusting agent (e.g., a salt such as sodium chloride), a pH buffer (e.g., citrate), and/or a sugar (e.g., glucose).

Engraftment of xenogeneic NK cells in an immunodeficient hu-IL-15 mouse is characterized by the presence of xenogeneic natural killer cells in the immunodeficient hu-IL-15 mouse. Presence of xenogeneic natural killer cells can be assessed by any of various methods, such as, but not limited to, flow cytometric analysis of cells in the animals to which the xenogeneic NK cells are administered at one or more time points following the administration of NK cells.

According to aspects of the present invention, the purified xenogeneic NK cells administered to an immunodeficient hu-IL-15 mouse are isolated from an original source material to obtain a population of cells enriched in NK cells. The purified xenogeneic NK cells may or may not be pure. According to aspects, xenogeneic NK cells are purified by selection for a cell marker, such as CD16 or CD56 and/or by depletion of non-NK cells, such as depletion of T cells by removal of CD3+ cells. According to aspects, administered purified xenogeneic NK cells are a population of cells in which CD16+ and/or CD56+ cells constitute about 25-100% of total cells. According to embodiments, administered purified xenogeneic NK cells are T cell depleted cells in which CD16+ and/or CD56+ cells make up about 25-100% of total cells or positively selected cells in which CD16+ and/or CD56+ NK cells make up about 90% or greater of total cells.

The number of administered purified xenogeneic NK cells is generally in the range of $1\times10^5$ to $1\times10^8$ (100,000 to 100,000,000) purified xenogeneic NK cells where the recipient is a mouse, although more or fewer can be used.

Thus, a method according to aspects of the present invention can include administering about $1\times10^5$ to $1\times10^8$ (100,000 to 100,000,000) purified xenogeneic NK cells, $10^5$ (100,000) to about $10^7$ (10,000,000), about $1\times10^5$ to about $1\times10^6$, about $5\times10^5$ to about $5\times10^6$, or about $1\times10^6$ to about $1\times10^7$, purified xenogeneic NK cells, such as purified human NK cells, to the immunodeficient hu-IL-15 mouse. The method can include administering at least about $1\times10^5$, about $2\times10^5$, about $3\times10^5$, about $4\times10^5$, about $5\times10^5$, about $6\times10^5$, about $7\times10^5$, about $8\times10^5$, about $9\times10^5$, about $1\times10^6$, about $2\times10^6$, about $3\times10^6$, about $4\times10^6$, about $5\times10^6$, about $6\times10^6$, about $7\times10^6$, about $8\times10^6$, about $9\times10^6$, about $1\times10^7$, about $2\times10^7$, about $3\times10^7$, about $4\times10^7$, about $5\times10^7$, about $6\times10^7$, about $7\times10^7$, about $8\times10^7$, about $9\times10^7$, or about $1\times10^8$, purified xenogeneic NK cells such as purified human NK cells, to the immunodeficient hu-IL-15 mouse. Those of ordinary skill will be able to determine a number of purified xenogeneic NK cells that should be administered to a specific mouse using no more than routine experimentation.

Successful engraftment can be detected by flow cytometry as 0.05% or greater xenogeneic CD16+ and/or CD56+ cells in the blood or spleen of the recipient immunodeficient hu-IL-15 mouse at 10-12 weeks after administration of the xenogeneic PBMCs.

Engraftment of purified xenogeneic NK cells in an immunodeficient hu-IL-15 mouse according to aspects of the present invention includes "conditioning" of the immunodeficient hu-IL-15 mouse prior to administration of the purified xenogeneic NK cells, for example by sub-lethal irradiation of the recipient animal with high frequency electromagnetic radiation, generally using gamma radiation, or treatment with a radiomimetic drug such as busulfan or nitrogen mustard. Conditioning is believed to reduce numbers of host hematopoietic cells, create appropriate microenvironmental factors for maintenance and/or production of NK cells, and/or create microenvironmental niches for maintenance and/or production of NK cells. Standard methods for conditioning are known in the art, such as described herein and in J. Hayakawa et al, 2009, Stem Cells, 27(1): 175-182.

Methods are provided according to aspects of the present invention which include administration of purified xenogeneic NK cells to an immunodeficient hu-IL-15 mouse without "conditioning" the immunodeficient hu-IL-15 mouse prior to administration of the purified xenogeneic NK cells. Methods are provided according to aspects of the present invention which include administration of purified xenogeneic NK cells to an immunodeficient hu-IL-15 mouse without "conditioning" by radiation or radiomimetic drugs of the immunodeficient hu-IL-15 mouse prior to administration of the purified xenogeneic NK cells.

Various aspects of the invention relate to administering purified xenogeneic NK cells to an immunodeficient hu-IL-15 mouse, producing an immunodeficient hu-IL-15 mouse having xenogeneic NK cells. Various aspects of the invention relate to administering purified human NK cells to an immunodeficient hu-IL-15 mouse, producing an immunodeficient hu-IL-15 mouse having human NK cells.

Administration of purified xenogeneic NK cells to an immunodeficient hu-IL-15 mouse results in the maintenance and/or production of xenogeneic natural killer cells in the mouse. Administration of purified human NK cells to an immunodeficient hu-IL-15 mouse results in the maintenance and/or production of human natural killer cells in the mouse.

Administration of purified xenogeneic NK cells to an immunodeficient hu-IL-15 mouse results in the maintenance and/or production of xenogeneic NK cells in the mouse that can be characterized by flow cytometry. For example, administration of human NK cells to an immunodeficient hu-IL-15 mouse results in the maintenance and/or production of natural killer cells in the mouse that can be characterized by flow cytometry, including human CD16+ and/or CD56+ human NK cells.

NK Cell Line Xenografts

Various aspects of the invention relate to administering xenogeneic immortalized natural killer cells (NK cell line cells) to an immunodeficient hu-IL-15 mouse, producing an immunodeficient hu-IL-15 mouse having xenogeneic NK cell line cells. The term "immortalized NK cell line cells" refers to NK cells which proliferate indefinitely due to one or more mutations by which the NK cells have escaped the cellular controls limiting their proliferative capacity, known as the Hayflick limit.

The xenogeneic NK cell line cells are human NK cell line cells according to aspects of the present invention.

NK cell line cells can be cells of a genetically engineered cell line. NK cell line cells can include a chimeric antigen receptor (CAR). NK cell line cells can be cells of a therapeutic NK cell line, including, but not limited to, NK-92. NK cell line cells can be any of various NK cell line cells including, but not limited to, cells of NK cell lines NK-92, NK-YS, KHYG-1, NKL, NKG, SNK-6 or IMC-1, all of which can be obtained from commercial and/or public cell repository sources (such as ATCC®), see Chen I M, et al., Leuk Res (2004) 28:275-84; Cheng M et al., Cell Transplant (2011) 20:1731-46; Gong J H, et al., Leukemia (1994) 8:652-8; Nagata H et al., Blood (2001) 97:708-13; Robertson M J, et al.,. Exp Hematol (1996) 24:406-15; Tsuchiyama J et al., Blood (1998) 92:1374-83; and Yagita M, et al., Leukemia (2000) 14:922-30.

Xenogeneic NK cell line cells can be administered into newborn mice by administration via various routes, such as, but not limited to, into the heart, liver and/or facial vein. Xenogeneic NK cell line cells can be administered into adult mice by various routes, such as, but not limited to, administration into the tail vein, into the femur bone marrow cavity or into the spleen. In a further example, fetal liver containing the xenogeneic NK cell line cells cells can be engrafted under the renal capsule.

Administering xenogeneic NK cell line cells to an immunodeficient hu-IL-15 mouse can include administering a composition comprising xenogeneic NK cell line cells to the immunodeficient hu-IL-15 mouse. The composition can further include, for example, water, a tonicity-adjusting agent (e.g., a salt such as sodium chloride), a pH buffer (e.g., citrate), and/or a sugar (e.g., glucose).

Presence of xenogeneic NK cell line cells can be assessed by any of various methods, such as, but not limited to, flow cytometric analysis of cells in the animals to which the xenogeneic NK cell line cells are administered at one or more time points following the administration of NK cell line cells.

The xenogeneic NK cell line cells may or may not be pure. According to embodiments, administered NK cell line cells make up about 90% or greater, 95% or greater, 99% or greater, or 100%, of total cells administered.

The number of xenogeneic NK cell line cells administered is not considered limiting. A single xenogeneic NK cell line cell can proliferate and generate sufficient NK cell line cells for detection of function. Thus, the number of administered xenogeneic NK cell line cells is generally in the range of $1\times10^3$ to $1\times10^6$ (1,000 to 1,000,000) xenogeneic NK cell line cells where the recipient is a mouse, although more or fewer can be used.

Thus, a method according to aspects of the present invention can include administering about $10^3$ (1000) to about $10^6$ (1,000,000), about $10^3$ to about $10^5$, about $10^4$ to about $10^6$, about $10^5$ to about $10^7$, about $1\times10^3$ to about $1\times10^4$, about $5\times10^3$ to about $5\times10^4$, about $1\times10^4$ to about $1\times10^5$, about $5\times10^4$ to about $5\times10^5$, about $1\times10^5$ to about $1\times10^6$, about $5\times10^5$ to about $5\times10^6$, about $1\times10^6$ to about $1\times10^7$, about $2\times10^4$ to about $5\times10^5$, or about $5\times10^4$ to about $2\times10^5$ xenogeneic NK cell line cells, such as human NK cell line cells, to the immunodeficient hu-IL-15 mouse. The method can include administering at least about $1\times10^2$, about $2\times10^2$, about $3\times10^2$, about $4\times10^2$, about $5\times10^2$, about $6\times10^2$, about $7\times10^2$, about $8\times10^2$, about $9\times10^2$, about $1\times10^3$, about $2\times10^3$, about $3\times10^3$, about $4\times10^3$, about $5\times10^3$, about $6\times10^3$, about $7\times10^3$, about $8\times10^3$, about $9\times10^3$, about $1\times10^4$, about $2\times10^4$, about $3\times10^4$, about $4\times10^4$, about $5\times10^4$, about $6\times10^4$, about $7\times10^4$, about $8\times10^4$, about $9\times10^4$, about $1\times10^5$, about $2\times10^5$, about $3\times10^5$, about $4\times10^5$, about $5\times10^5$, about $6\times10^5$, about $7\times10^5$, about $8\times10^5$, about $9\times10^5$, about $1\times10^6$, about $2\times10^6$, about $3\times10^6$, about $4\times10^6$, about $5\times10^6$, about $6\times10^6$, about $7\times10^6$, about $8\times10^6$, about $9\times10^6$, or about $1\times10^7$ xenogeneic NK cell line cells, such as human NK cell line cells, to the immunodeficient hu-IL-15 mouse. The method can include administering about $1\times10^2$, about $2\times10^2$, about $3\times10^2$, about $4\times10^2$, about $5\times10^2$, about $6\times10^2$, about $7\times10^2$, about $8\times10^2$, about $9\times10^2$, about $1\times10^3$, about $2\times10^3$, about $3\times10^3$, about $4\times10^3$, about $5\times10^3$, about $6\times10^3$, about $7\times10^3$, about $8\times10^3$, about $9\times10^3$, about $1\times10^4$, about $2\times10^4$, about $3\times10^4$, about $4\times10^4$, about $5\times10^4$, about $6\times10^4$, about $7\times10^4$, about $8\times10^4$, about $9\times10^4$, about $1\times10^5$, about $2\times10^5$, about $3\times10^5$, about $4\times10^5$, about $5\times10^5$, about $6\times10^5$, about $7\times10^5$, about $8\times10^5$, about $9\times10^5$, about $1\times10^6$, about $2\times10^6$, about $3\times10^6$, about $4\times10^6$, about $5\times10^6$, about $6\times10^6$, about $7\times10^6$, about $8\times10^6$, about $9\times10^6$, or about $1\times10^7$ xenogeneic NK cell line cells, such as human NK cell line cells, to the immunodeficient hu-IL-15 mouse. Those of ordinary skill will be able to determine a number of xenogeneic HSC that should be administered to a specific mouse using no more than routine experimentation.

Successful engraftment can be detected by flow cytometry as 0.05% or greater xenogeneic NK cell line cells in the blood or spleen of the recipient immunodeficient hu-IL-15 mouse at 10-12 weeks after administration of the xenogeneic.

Engraftment of xenogeneic NK cell line cells in an immunodeficient hu-IL-15 mouse according to aspects of the present invention includes "conditioning" of the immunodeficient hu-IL-15 mouse prior to administration of the xenogeneic NK cell line cells, for example by sub-lethal irradiation of the recipient animal with high frequency electromagnetic radiation, generally using gamma radiation, or treatment with a radiomimetic drug such as busulfan or nitrogen mustard. Conditioning is believed to reduce numbers of host hematopoietic cells, create appropriate microenvironmental factors for maintenance and/or production of xenogeneic NK cell line cells and/or create microenvironmental niches for maintenance and/or production of xenogeneic NK cell line cells. Standard methods for conditioning are known in the art, such as described herein and in J. Hayakawa et al, 2009, Stem Cells, 27(1):175-182.

Methods are provided according to aspects of the present invention which include administration of xenogeneic NK cell line cells to an immunodeficient hu-IL-15 mouse without "conditioning" the immunodeficient hu-IL-15 mouse prior to administration of the xenogeneic NK cell line cells. Methods are provided according to aspects of the present invention which include administration of xenogeneic NK cell line cells to an immunodeficient hu-IL-15 mouse without "conditioning" by radiation or radiomimetic drugs of the immunodeficient hu-IL-15 mouse prior to administration of the xenogeneic NK cell line cells.

Various aspects of the invention relate to administering xenogeneic NK cell line cells to an immunodeficient hu-IL-15 mouse, producing an immunodeficient hu-IL-15 mouse having xenogeneic NK cell line cells. Various aspects of the invention relate to administering human NK cell line cells to an immunodeficient hu-IL-15 mouse, producing an immunodeficient hu-IL-15 mouse having human NK cell line cells.

Administration of xenogeneic NK cell line cells to an immunodeficient hu-IL-15 mouse results in the maintenance and/or production of xenogeneic NK cell line cells in the mouse. Administration of human NK cell line cells to an immunodeficient hu-IL-15 mouse results in the maintenance and/or production of human NK cell line cells in the mouse.

Administration of xenogeneic NK cell line cells to an immunodeficient hu-IL-15 mouse results in the maintenance and/or production of xenogeneic NK cell line cells in the mouse that can be characterized by flow cytometry. For example, administration of human NK cell line cells NK cells to an immunodeficient hu-IL-15 mouse results in the maintenance and/or production of xenogeneic NK cell line cells in the mouse that can be characterized by flow cytometry.

Tumor Xenograft

Various aspects of the invention relate to administering xenogeneic tumor cells to an immunodeficient hu-IL-15 mouse.

Xenogeneic tumor cells administered to immunodeficient hu-IL-15 mice of the present invention can be any of various tumor cells, including but not limited to, cells of a tumor cell line and primary tumor cells. The xenogeneic tumor cells may be derived from any of various organisms, preferably mammalian, including human, non-human primate, rat, guinea pig, rabbit, cat, dog, horse, cow, goat, pig and sheep.

According to specific aspects of the present invention, the xenogeneic tumor cells are human tumor cells. According to specific aspects of the present invention, the human tumor cells are present in a sample obtained from the human, such as, but not limited to, in a blood sample, tissue sample, or sample obtained by biopsy of a human tumor.

Tumor cells obtained from a human can be administered directly to an immunodeficient hu-IL-15 mouse of the present invention or may be cultured in vitro prior to administration to the immunodeficient hu-IL-15 mouse.

As used herein, the term "tumor" refers to cells characterized by unregulated growth including, but not limited to, pre-neoplastic hyperproliferation, cancer in-situ, neoplasms, metastases and solid and non-solid tumors. Examples of tumors are those caused by cancer include, but are not limited to, lymphoma, leukemia, squamous cell cancer, small-cell lung cancer, non-small cell lung cancer, adenocarcinoma of the lung, squamous carcinoma of the lung, cancer of the peritoneum, adrenal cancer, anal cancer, bile duct cancer, bladder cancer, brain cancer, breast cancer, triple negative breast cancer, central or peripheral nervous system cancers, cervical cancer, colon cancer, colorectal cancer, endometrial cancer, esophageal cancer, gall bladder cancer, gastrointestinal cancer, glioblastoma, head and neck cancer, kidney cancer, liver cancer, nasopharyngeal cancer, nasal cavity cancer, oropharyngeal cancer, oral cavity cancer, osteosarcoma, ovarian cancer, pancreatic cancer, parathyroid cancer, pituitary cancer, prostate cancer, retinoblastoma, sarcoma, salivary gland cancer, skin cancer, small intestine cancer, stomach cancer, testicular cancer, thymus cancer, thyroid cancer, uterine cancer, vaginal cancer and vulval cancer.

Administering the tumor cells to the immunodeficient hu-IL-15 mouse can be any method that is suitable as recognized in the art. For example, administration can include administering cells into an organ, body cavity, or blood vessel such as by injection or implantation, such as subcutaneous and/or intraperitoneal implantation. The tumor cells may be administered as a tumor mass, clumps of tumor cells or as dissociated cells.

Tumor cells can be administered by various routes, such as, but not limited to, by subcutaneous injection, intraperitoneal injection or injection into the tail vein.

Engraftment of xenogeneic tumor cells can be assessed by any of various methods, such as, but not limited to, visual inspection of the mouse for signs of tumor formation.

Any of various methods can be used to measure growth of xenogeneic tumors, including but not limited to, measurement in living mice, measurement of tumors excised from living mice or measurement of tumors in situ or excised from dead mice. Measurements can be obtained using a measuring instrument such as a caliper, measurement using one or more imaging techniques such as ultrasonography, computed tomography, positron emission tomography, fluorescence imaging, bioluminescence imaging, magnetic resonance imaging and combinations of any two or more of these or other tumor measurement methods. The number of tumor cells in a sample obtained from a mouse bearing xenogeneic tumor cells can be used to measure tumor growth, particularly for non-solid tumors. For example, the number of non-solid tumor cells in a blood sample can be assessed to obtain a measurement of growth of a non-solid tumor in a mouse.

The number of tumor cells administered is not considered limiting. A single tumor cell can expand into a detectable tumor in the genetically modified immunodeficient animals described herein. The number of administered tumor cells is generally in the range of 1000-1,000,000 tumor cells, although more or fewer can be administered.

Thus, a method according to aspects of the present invention can include administering about $10^2$ (100) to about $10^7$ (10,000,000), about $10^3$ to about $10^5$, about $10^4$ to about $10^6$, about $10^5$ to about $10^7$, about $1\times10^3$ to about $1\times10^4$, about $5\times10^3$ to about $5\times10^4$, about $1\times10^4$ to about $1\times10^5$, about $5\times10^4$ to about $5\times10^5$, about $1\times10^5$ to about $1\times10^6$, about $5\times10^5$ to about $5\times10^6$, about $1\times10^6$ to about $1\times10^7$, about $2\times10^4$ to about $5\times10^5$, or about $5\times10^4$ to about $2\times10^5$ xenogeneic tumor cells, such as human tumor cells, to the immunodeficient hu-IL-15 mouse. The method can include administering at least about $1\times10^2$, about $2\times10^2$, about $3\times10^2$, about $4\times10^2$, about $5\times10^2$, about $6\times10^2$, about $7\times10^2$, about $8\times10^2$, about $9\times10^2$, about $1\times10^3$, about $2\times10^3$, about $3\times10^3$, about $4\times10^3$, about $5\times10^3$, about $6\times10^3$, about $7\times10^3$, about $8\times10^3$, about $9\times10^3$, about $1\times10^4$, about $2\times10^4$, about $3\times10^4$, about $4\times10^4$, about $5\times10^4$, about $6\times10^4$, about $7\times10^4$, about $8\times10^4$, about $9\times10^4$, about $1\times10^5$, about $2\times10^5$, about $3\times10^5$, about $4\times10^5$, about $5\times10^5$, about $6\times10^5$, about $7\times10^5$, about $8\times10^5$, about $9\times10^5$, about $1\times10^6$, about $2\times10^6$, about $3\times10^6$, about $4\times10^6$, about $5\times10^6$, about $6\times10^6$, about $7\times10^6$, about $8\times10^6$, about $9\times10^6$, or about $1\times10^7$ xenogeneic tumor cells, such as human tumor cells, to the immunodeficient hu-IL-15 mouse. The method can include administering about $1\times10^2$, about $2\times10^2$, about $3\times10^2$, about $4\times10^2$, about $5\times10^2$, about $6\times10^2$, about $7\times10^2$, about $8\times10^2$, about $9\times10^2$, about $1\times10^3$, about $2\times10^3$, about $3\times10^3$, about $4\times10^3$, about $5\times10^3$, about $6\times10^3$, about $7\times10^3$, about $8\times10^3$, about $9\times10^3$, about $1\times10^4$, about $2\times10^4$, about $3\times10^4$, about $4\times10^4$, about $5\times10^4$, about $6\times10^4$, about $7\times10^4$, about $8\times10^4$, about $9\times10^4$, about $1\times10^5$, about $2\times10^5$, about $3\times10^5$, about $4\times10^5$, about $5\times10^5$, about $6\times10^5$, about $7\times10^5$, about $8\times10^5$, about $9\times10^5$, about $1\times10^6$, about $2\times10^6$, about $3\times10^6$, about $4\times10^6$, about $5\times10^6$, about $6\times10^6$, about $7\times10^6$, about $8\times10^6$, about $9\times10^6$, or about $1\times10^7$ xenogeneic tumor cells, such as human tumor cells, to the immunodeficient hu-IL-15 mouse. Those of ordinary skill will be able to determine a number of xenogeneic tumor cells that should be administered to a specific mouse using no more than routine experimentation.

According to aspects of the present invention, xenogeneic tumor cells, and xenogeneic HSC and/or xenogeneic PBMCs, are administered to an immunodeficient hu-IL-15 mouse. The xenogeneic tumor cells, and xenogeneic HSC and/or xenogeneic PBMCs, can be administered at the same time or at different times.

According to aspects of the present invention, the xenogeneic tumor cells are derived from the same species as the administered HSC and/or xenogeneic PBMCs. According to aspects, the tumor cells and the HSC and/or xenogeneic PBMCs administered to an immunodeficient hu-IL-15 mouse are human cells.

According to aspects of the present invention the administered HSC and/or xenogeneic PBMCs and tumor cells are human leukocyte antigen (HLA) matched (e.g., MHC Class I matched and/or MHC class II matched). HLA-matching may reduce the likelihood of a graft-versus-graft immune response against HLA cell-surface proteins. An immune response against HLA may falsely suggest that xenogeneic immune cells are successfully targeting xenogeneic cancer cells.

The administered HSC and/or xenogeneic PBMCs, and the administered tumor cells can include at least 2, 3, 4, 5, 6, 7, 8, 9, 10, 11, 12, 13, 14, 15, 16, 17, 18, 19, or 20 matching HLA alleles. The administered HSC and/or xenogeneic PBMCs, and the tumor cells, can include at least 2, 3, 4, 5, 6, 7, or 8 matching HLA alleles selected from the alleles for HLA-A, HLA-B, HLA-C, and HLA-DRB1. Perfect HLA matching is rarely possible without genetic engineering, and perfect HLA matching may be unnecessary. Control experiments, for example, can account for any HLA-mediated graft-versus-graft immune response.

Assay Methods

Methods and immunodeficient hu-IL-15 mice provided according to aspects of the present invention have various utilities such as, in vivo testing of substances directed against human cancer.

Methods for identifying anti-tumor activity of a test substance according to aspects of the present invention include providing an immunodeficient hu-IL-15 mouse; administering xenogeneic tumor cells to the immunodeficient hu-IL-15 mouse, wherein the xenogeneic tumor cells form a solid or non-solid tumor in the immunodeficient hu-IL-15 mouse; administering a test substance to the immunodeficient hu-IL-15 mouse; assaying a response of the xenogeneic tumor and/or tumor cells to the test substance, wherein an inhibitory effect of the test substance on the tumor and/or tumor cells identifies the test substance as having anti-tumor activity.

Methods for identifying anti-tumor activity of a test substance according to aspects of the present invention include providing an immunodeficient hu-IL-15 mouse, wherein the immunodeficient hu-IL-15 mouse has engrafted xenogeneic HSC; administering xenogeneic tumor cells to the immunodeficient hu-IL-15 mouse, wherein the xenogeneic tumor cells form a solid or non-solid tumor in the immunodeficient hu-IL-15 mouse; administering a test substance to the immunodeficient hu-IL-15 mouse; assaying a response of the xenogeneic tumor and/or tumor cells to the test substance, wherein an inhibitory effect of the test substance on the tumor and/or tumor cells identifies the test substance as having anti-tumor activity.

Methods for identifying anti-tumor activity of a test substance according to aspects of the present invention include providing an immunodeficient hu-IL-15 mouse, wherein the immunodeficient hu-IL-15 mouse has engrafted human HSC; administering human tumor cells to the immunodeficient hu-IL-15 mouse, wherein the human tumor cells form a solid or non-solid tumor in the immunodeficient hu-IL-15 mouse; administering a test substance to the immunodeficient hu-IL-15 mouse; assaying a response of the human tumor and/or tumor cells to the test substance, wherein an inhibitory effect of the test substance on the tumor and/or tumor cells identifies the test substance as having anti-tumor activity.

An immunodeficient hu-IL-15 mouse used in an assay for identifying anti-tumor activity of a test substance according to aspects of the present invention is an NSG-hu-IL-15 mouse, an NRG-hu-IL-15 mouse or a NOG-hu-IL-15 mouse.

The term "inhibitory effect" as used herein refers to an effect of the test substance to inhibit one or more of: tumor growth, tumor cell metabolism and tumor cell division.

Assaying a response of the xenogeneic tumor and/or tumor cells to the test substance includes comparing the response to a standard to determine the effect of the test substance on the xenogeneic tumor cells according to aspects of methods of the present invention, wherein an inhibitory effect of the test substance on the xenogeneic tumor cells identifies the test substance as an anti-tumor composition. Standards are well-known in the art and the standard used can be any appropriate standard. In one example, a standard is a compound known to have an anti-tumor effect. In a further example, non-treatment of a comparable xenogeneic tumor provides a base level indication of the tumor growth without treatment for comparison of the effect of a test substance. A standard may be a reference level of expected tumor growth previously determined in an individual comparable mouse or in a population of comparable mice and stored in a print or electronic medium for recall and comparison to an assay result.

Assay results can be analyzed using statistical analysis by any of various methods to determine whether the test substance has an inhibitory effect on a tumor, exemplified by parametric or non-parametric tests, analysis of variance, analysis of covariance, logistic regression for multivariate analysis, Fisher's exact test, the chi-square test, Student's T-test, the Mann-Whitney test, Wilcoxon signed ranks test, McNemar test, Friedman test and Page's L trend test. These and other statistical tests are well-known in the art as detailed in Hicks, CM, Research Methods for Clinical Therapists: Applied Project Design and Analysis, Churchill Livingstone (publisher); 5th Ed., 2009; and Freund, R J et al., Statistical Methods, Academic Press; 3rd Ed., 2010.

A test substance used in a method of the present invention can be any chemical entity, illustratively including a synthetic or naturally occurring compound or a combination of a synthetic or naturally occurring compound, a small organic or inorganic molecule, a protein, a peptide, a nucleic acid, a carbohydrate, an oligosaccharide, a lipid or a combination of any of these. According to aspects of the present invention, the test substance is an immunotherapeutic.

According to aspects of the present invention, a test substance is an anti-cancer agent. According to aspects of the present invention, the test substance is an anti-cancer immunotherapeutic, such as an anti-cancer antibody or antigen binding fragment thereof.

Anti-cancer agents are described, for example, in Brunton et al. (eds.), Goodman and Gilman's The Pharmacological Basis of Therapeutics, 12th Ed., Macmillan Publishing Co., 2011.

Anti-cancer agents illustratively include acivicin, aclarubicin, acodazole, acronine, adozelesin, aldesleukin, alitretinoin, allopurinol, altretamine, ambomycin, ametantrone, amifostine, aminoglutethimide, amsacrine, anastrozole, anthramycin, arsenic trioxide, asparaginase, asperlin, azacitidine, azetepa, azotomycin, batimastat, benzodepa, bicalutamide, bisantrene, bisnafide dimesylate, bizelesin, bleomycin, brequinar, bropirimine, busulfan, cactinomycin, calusterone, capecitabine, caracemide, carbetimer, carboplatin, carmustine, carubicin, carzelesin, cedefingol, celecoxib, chlorambucil, cirolemycin, cisplatin, cladribine, cobimetinib, crisnatol mesylate, cyclophosphamide, cytarabine, dacarbazine, dactinomycin, daunorubicin, decitabine, dexormaplatin, dezaguanine, dezaguanine mesylate, diaziquone, docetaxel, doxorubicin, droloxifene, dromostanolone, duazomycin, edatrexate, eflomithine, elsamitrucin, enloplatin, enpromate, epipropidine, epirubicin, erbulozole, esorubicin, estramustine, etanidazole, etoposide, etoprine, fadrozole, fazarabine, fenretinide, floxuridine, fludarabine, fluorouracil, flurocitabine, fosquidone, fostriecin, fulvestrant, gemcitabine, hydroxyurea, idarubicin, ifosfamide, ilmofosine, interleukin II (IL-2, including recombinant interleukin II or rIL2), interferon alfa-2a, interferon alfa-2b, interferon alfa-n1, interferon alfa-n3, interferon beta-Ia, interferon gamma-Ib, iproplatin, irinotecan, lanreotide, letrozole, leuprolide, liarozole, lometrexol, lomustine, losoxantrone, masoprocol, maytansine, mechlorethamine hydrochlride, megestrol, melengestrol acetate, melphalan, menogaril, mercaptopurine, methotrexate, metoprine, meturedepa, mitindomide, mitocarcin, mitocromin, mitogillin, mitomalcin, mitomycin, mitosper, mitotane, mitoxantrone, mycophenolic acid, nelarabine, nocodazole, nogalamycin, ormnaplatin, oxisuran, paclitaxel, pegaspargase, peliomycin, pentamustine, peplomycin, perfosfamide, pipobroman, piposulfan, piroxantrone hydrochloride, plicamycin, plomestane, porfimer, porfiromycin, prednimustine, procarbazine, puromycin, pyrazofurin, riboprine, rogletimide, safingol, semustine, simtrazene, sparfosate, sparsomycin, spirogermanium, spiromustine, spiroplatin, streptonigrin, streptozocin, sulofenur, talisomycin, tamoxifen, tecogalan, tegafur, teloxantrone, temoporfin, teniposide, teroxirone, testolactone, thiamiprine, thioguanine, thiotepa, tiazofurin, tirapazamine, topotecan, toremifene, trestolone, triciribine, trimetrexate, triptorelin, tubulozole, uracil mustard, uredepa, vapreotide, vemurafenib, verteporfin, vinblastine, vincristine sulfate, vindesine, vinepidine, vinglycinate, vinleurosine, vinorelbine, vinrosidine, vinzolidine, vorozole, zeniplatin, zinostatin, zoledronate, and zorubicin.

According to aspects of the present invention, an anti-cancer agent is an anti-cancer antibody. An anti-cancer antibody used can be any antibody effective to inhibit at least one type of tumor, particularly a human tumor. Anti-cancer antibodies include, but are not limited to, 3F8, 8H9, abagovomab, abituzumab, adalimumab, adecatumumab, aducanumab, afutuzumab, alacizumab pegol, alemtuzumab, amatuximab, anatumomab mafenatox, anetumab ravtansine, apolizumab, arcitumomab, ascrinvacumab, atezolizumab, bavituximab, belimumab, bevacizumab, bivatuzumab mertansine, brentuximab vedotin, brontictuzumab, cantuzumab mertansine, cantuzumab ravtansine, capromab pendetide, catumaxomab, cetuximab, citatuzumab bogatox, cixutumumab, clivatuzumab tetraxetan, coltuximab ravtansine, conatumumab, dacetuzumab, dalotuzumab, demcizumab, denintuzumab mafodotin, depatuxizumab mafodotin, durvalumab, dusigitumab, edrecolomab, elotuzumab, emactuzumab, emibetuzumab, enoblituzumab, enfortumab vedotin, enavatuzumab, epratuzumab, ertumaxomab, etaracizumab, farletuzumab, ficlatuzumab, figitumumab, flanvotumab, futuximab, galiximab, ganitumab, gemtuzumab, girentuximab, glembatumumab vedotin, ibritumomab tiuxetan, igovomab, imab362, imalumab, imgatuzumab, indatuximab ravtansine, indusatumab vedotin, inebilizumab, inotuzumab ozogamicin, intetumumab, ipilimumab, iratumumab, isatuximab, labetuzumab, lexatumumab, lifastuzumab vedotin, lintuzumab, lirilumab, lorvotuzumab mertansine, lucatumumab, lumiliximab, lumretuzumab, mapatumumab, margetuximab, matuzumab, milatuzumab, mirvetuximab soravtansine, mitumomab, mogamulizumab, moxetumomab pasudotox, nacolomab tafenatox, naptumomab estafenatox, narnatumab, necitumumab, nesvacumab, nimotuzumab, nivolumab, ocaratuzumab, ofatumumab, olaratumab, onartuzumab, ontuxizumab, oregovomab, oportuzumab monatox, otlertuzumab, panitumumab, pankomab, parsatuzumab, patritumab, pembrolizumab, pemtumomab, pertuzumab, pidilizumab, pinatuzumab vedotin, polatuzumab vedotin, pritumumab, racotumomab, radretumab, ramucirumab, rilotumumab, rituximab, robatumumab, sacituzumab govitecan, samalizumab, seribantumab, sibrotuzumab, siltuximab, sofituzumab vedotin, tacatuzumab tetraxetan, tarextumab, tenatumomab, teprotumumab, tetulomab, tigatuzumab, tositumomab, tovetumab, trastuzumab, tremelimumab, tucotuzumab celmoleukin, ublituximab, utomilumab, vandortuzumab vedotin, vantictumab, vanucizumab, varlilumab, vesencumab, volociximab, vorsetuzumab mafodotin, votumumab, zalutumumab and zatuximab.

According to aspects of the present invention, a test substance is one that specifically binds one or more of: 1) a cell-surface protein such as a cluster of differentiation (CD) cell-surface molecule; 2) an intracellular protein such as a kinase; and 3) an extracellular protein such as a shed cell-surface receptor or the soluble ligand of a cell-surface receptor.

According to aspects of the present invention, a test substance is one that specifically binds a protein that is expressed by leukocytes (e.g., lymphocytes or myeloid-lineage leukocytes). In a further option, a test substance is one that specifically binds a ligand of a leukocyte. In a still further option, a test substance is one that specifically binds a molecule that is expressed by a cancer cell.

According to aspects of the present invention, a test substance is a chemotherapeutic agent or an immunotherapeutic agent. According to aspects of the present invention, a test substance can specifically binds PD-1, PD-L1, or CTLA-4. According to aspects of the present invention, a test substance can be an immune checkpoint inhibitor such as a PD-1 inhibitor, PD-L1 inhibitor, or CTLA-4 inhibitor. According to aspects of the present invention, a test substance is an immune checkpoint inhibitor selected from atezolizumab, avelumab, durvalumab, ipilimumab, nivolumab, pembrolizumab, and an antigen-binding fragment of any one of the foregoing.

The test substance can be administered by any suitable route of administration, such as, but not limited to, oral, rectal, buccal, nasal, intramuscular, vaginal, ocular, otic, subcutaneous, transdermal, intratumoral, intravenous, and intraperitoneal.

Embodiments of inventive compositions and methods are illustrated in the following examples. These examples are provided for illustrative purposes and are not considered limitations on the scope of inventive compositions and methods.

EXAMPLES

Creation of Human IL-15 Transgenic NSG Mice

A ~200Kbp BAC, designated RP11-620F3, containing the human IL15 gene, was purchased from Chori BACPAC. Pronuclear injection of NSG embryos yielded a transgenic male founder that transmitted the human IL15 gene to his offspring. NSG-Tg(Hu-IL15) hemizygous offspring were identified by polymerase chain reaction (PCR) and the colony was expanded. Human IL-15 levels were first ascertained on the NSG-Tg(Hu-IL15) hemizygotes. Plasma was collected from three female mice hemizygous for the human IL-15 transgene and three female NSG non-transgenic mice, age 55 days. ELISA assays used Quantikine human IL-15 ELISA kits (R&D Systems, Minneapolis, MN). The NSG-Tg(Hu-IL15) hemizgotes had physiological levels of human IL-15 (7.1+/−0.3 μg/ml) while the non-transgenic NSG mice, as expected, lacked human IL-15, documenting the production of human IL-15 protein in the transgenic animals (FIG. 1).

Figure 2:
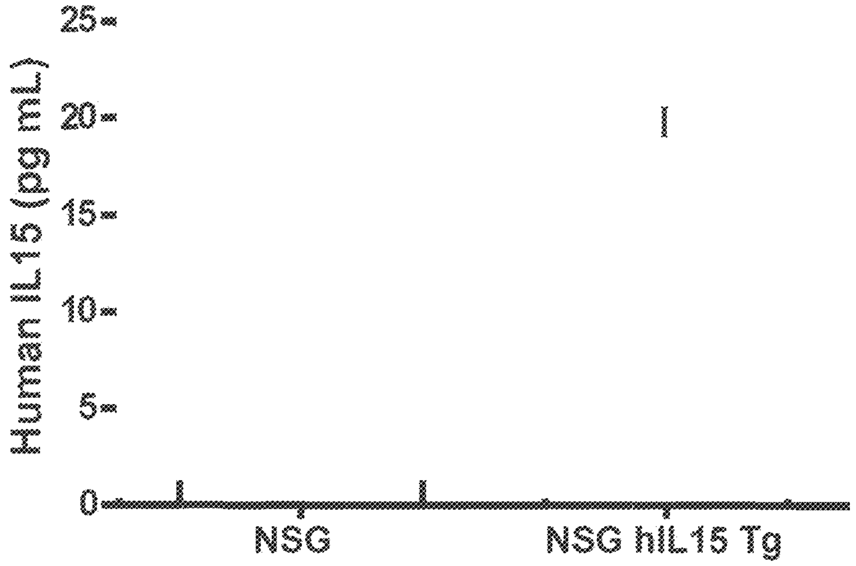
FIG. 2 is a graph showing human IL15 levels in sera from NSG-Tg(Hu-IL15) homozygotes

Subsequent crosses and test matings produced additional NSG-Tg(Hu-IL15) offspring. Genetic crosses were performed to fix the human IL-15 transgene to homozygosity and it was found that the Hu-IL15 transgenic homozygotes survived well and bred in matings of homozygotes. The NSG-Tg(Hu-IL15) colony is maintained in a high-barrier mouse room by sib matings. The homozygous expression of the human IL15 transgene results in two-fold higher levels of human IL-15 compared with the NSG-Tg(Hu-IL15) hemizygotes (FIG. 2). Immunocompetent mice transgenically overexpressing murine IL-15 are described in T. A. Fehniger et al., Fatal leukemia in interleukin-15 transgenic mice, Blood cells, molecules & diseases 27, 223-230 (2001), and these mouse IL-15 transgenic animals develop a fatal lymphocytic leukemia with a T-NK cell phenotype starting by 6 weeks of age. In contrast, NSG-Tg(Hu-IL15) mice lack endogenous murine T and NK cells and do not develop mouse leukemia. NSG-Tg(Hu-IL15) homozygous breeding pairs are routinely kept in a breeding colony for 6-9 months before they are retired due to decreasing breeding efficiency and no evidence of leukemia has been found.

NSG-Tg (Hu-IL15) Mice Support Human NK Cell Development

Figure 3:
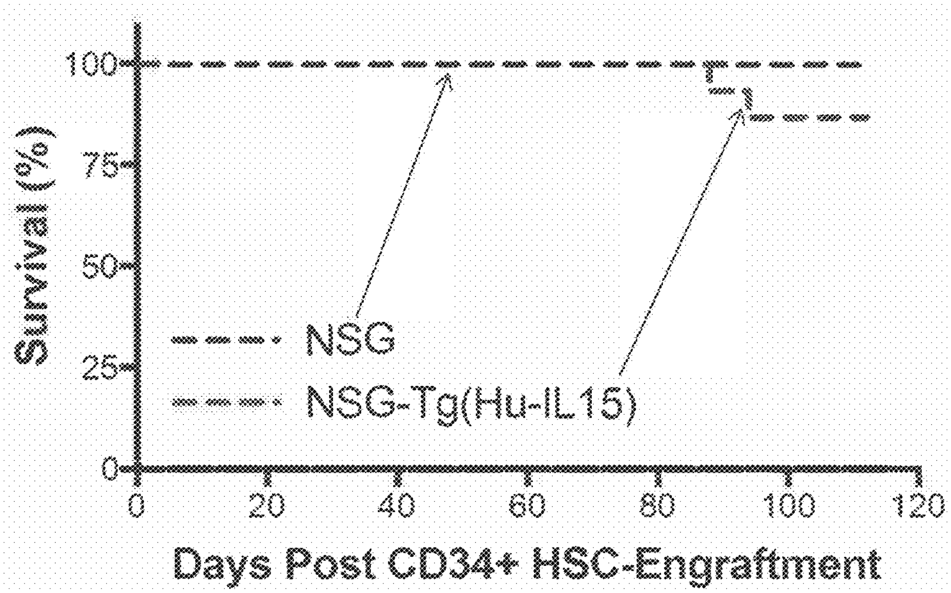
FIG. 3 is a graph showing that HSC-engrafted NSG-Tg (Hu-IL15) mice have similar survival compared to HSC-engrafted NSG mice. For this study, NSG or NSG-Tg(Hu-IL15) mice (6 to 8 weeks of age) were irradiated (200 cGy) and injected intravenously (IV) with 100,000 CD34+ HSC derived from umbilical cord blood. Survival was monitored for both groups of mice.
Figure 4:
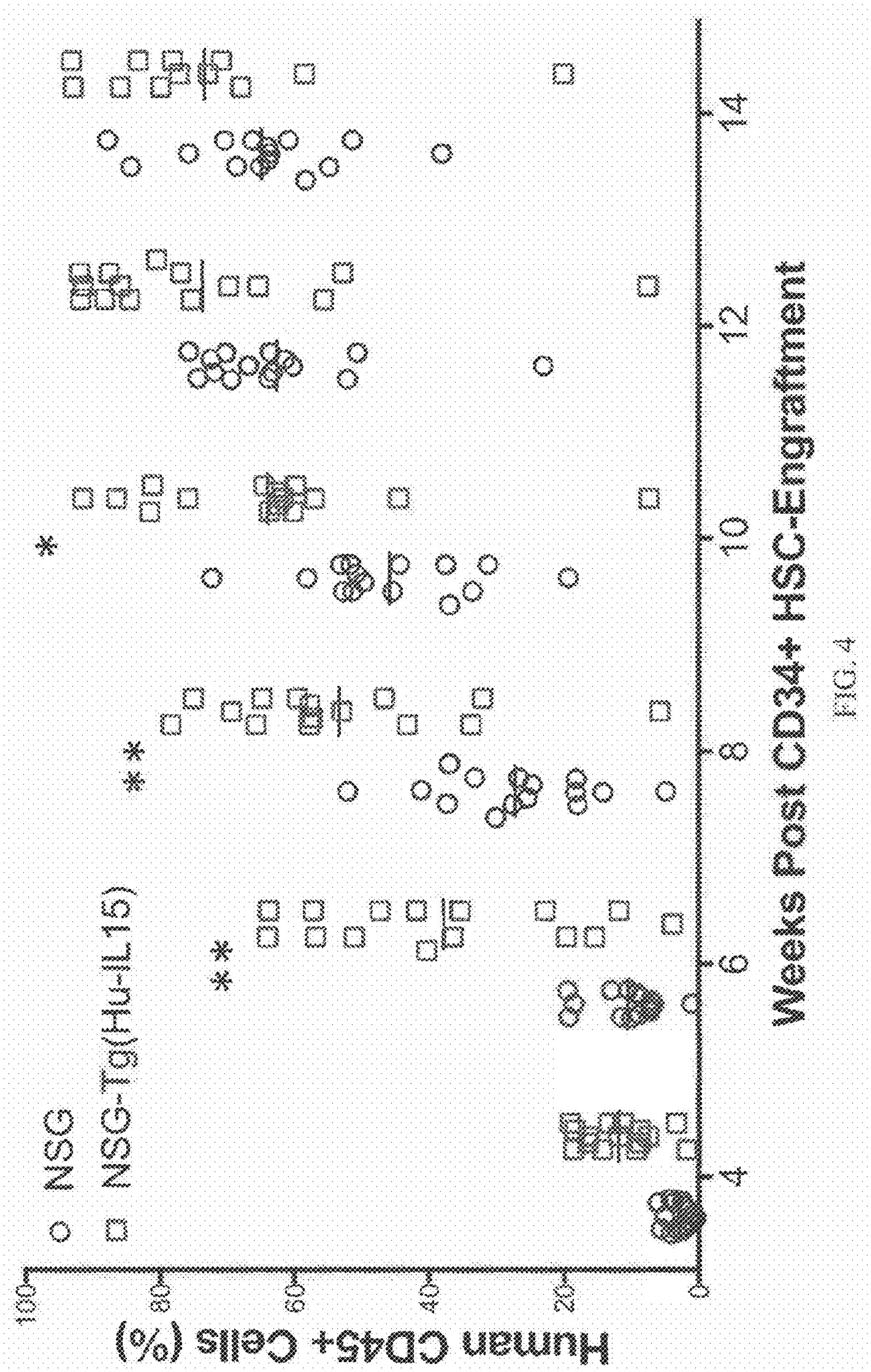
FIG. 4 is a graph showing that HSC-engrafted NSG-Tg (Hu-IL15) mice have accelerated development of CD45+ cells in blood. For this study, NSG or NSG-Tg(Hu-IL15) mice (6 to 8 weeks of age) were irradiated (200 cGy) and injected IV with 100,000 CD34+ HSC derived from umbilical cord blood. Levels of human CD45+ cells were monitored in the peripheral blood by flow cytometry.
Figure 5:
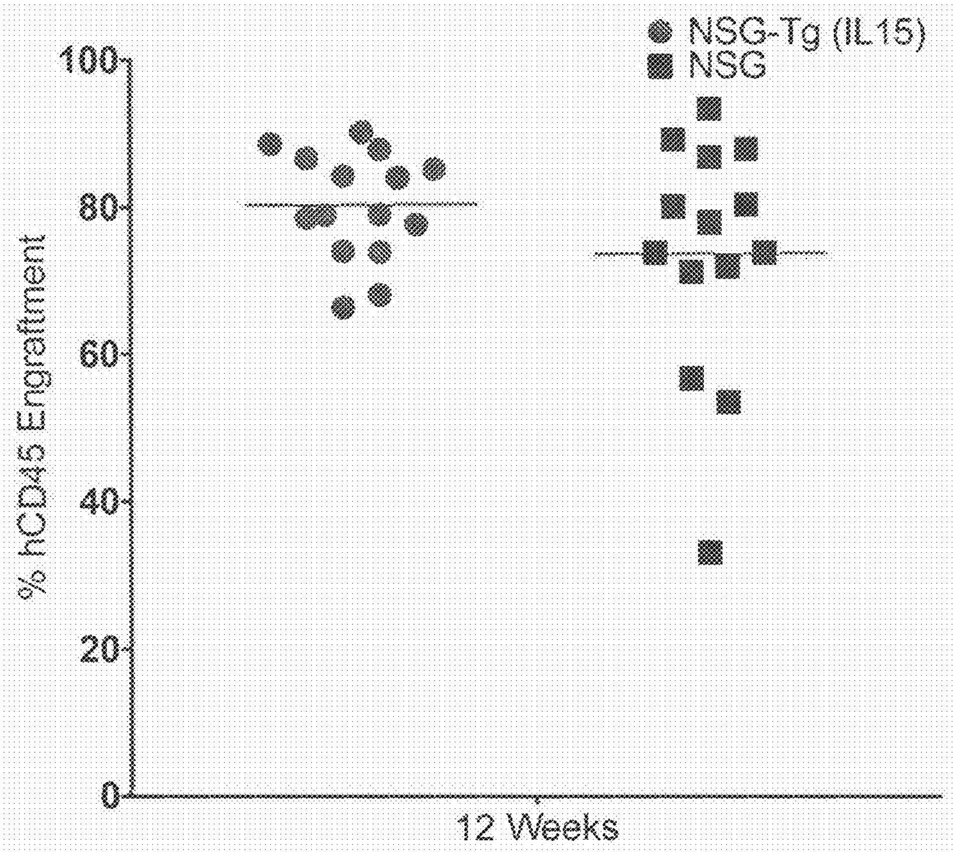
FIG. 5 is a graph showing % hCD45 engraftment in NSG-Tg(Hu-IL15) mice compared to NSG mice.

In order to determine whether NSG-Tg(Hu-IL15) mice will support the development of human NK cells following engraftment with human hematopoietic stem cells (HSC), groups of 8 to 12-week-old NSG-Tg(HuIL15) mice along with age and sex-matched NSG controls were engrafted with human HSC. Briefly, recipient mice received 200 cGy irradiation and were then injected intravenously with 1×10$^5$ human CD34+ HSC enriched from umbilical cord blood. Human NK cell development and phenotype were monitored using flow cytometry. Human HSC engrafted NSG and NSG-Tg(Hu-IL15) mice have similar levels of survival over the course of the experiment (FIG. 3). Levels of human CD45+ cells were monitored in the peripheral blood by flow cytometry. NSG-Tg(Hu-IL15) mice have accelerated development of CD45+ cells in blood compared to NSG mice, as shown in FIG. 4. Human leukocyte development, as determined by the levels of human CD45+ cells, is similar in the peripheral blood of NSG and NSG-Tg(Hu-IL15) mice at all time points tested, with representative data at 12 weeks post-HSC injection shown in FIG. 5.

Figure 6:
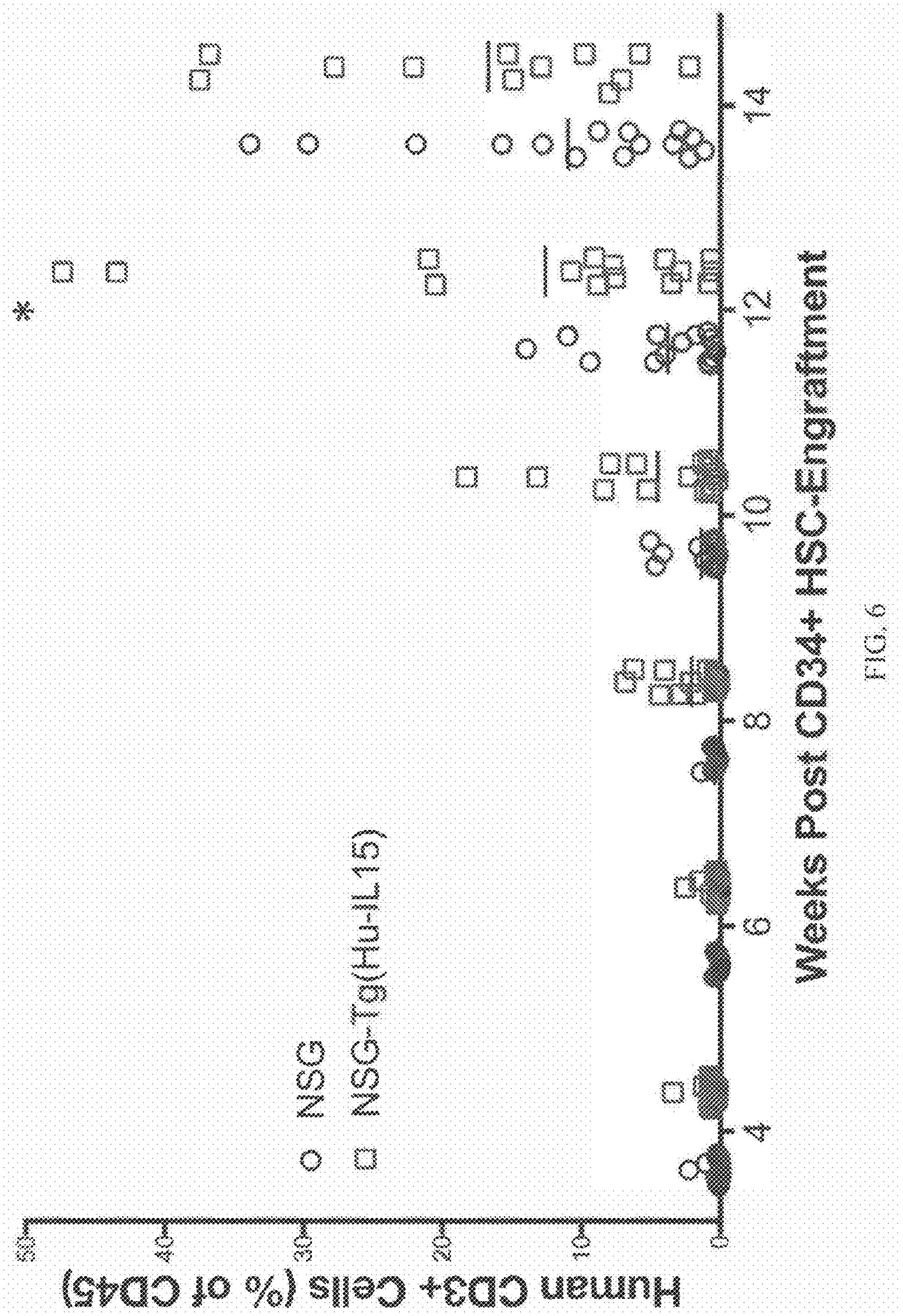
FIG. 6 is a graph showing HSC-Engrafted NSG-Tg(Hu-IL15) mice show similar development of human T cells in blood. For this study, NSG or NSG-Tg(Hu-IL15) mice (6 to 8 weeks of age) were irradiated (200 cGy) and injected IV with 100,000 CD34+ HSC derived from umbilical cord blood. Levels of human CD3+ T cells were monitored in the peripheral blood by flow cytometry.

Levels of human CD3+ T cells were monitored in the peripheral blood by flow cytometry. HSC-Engrafted NSG-Tg(Hu-IL15) mice show similar development of human T cells in blood compared to NSG mice, see FIG. 6.

Figure 7:
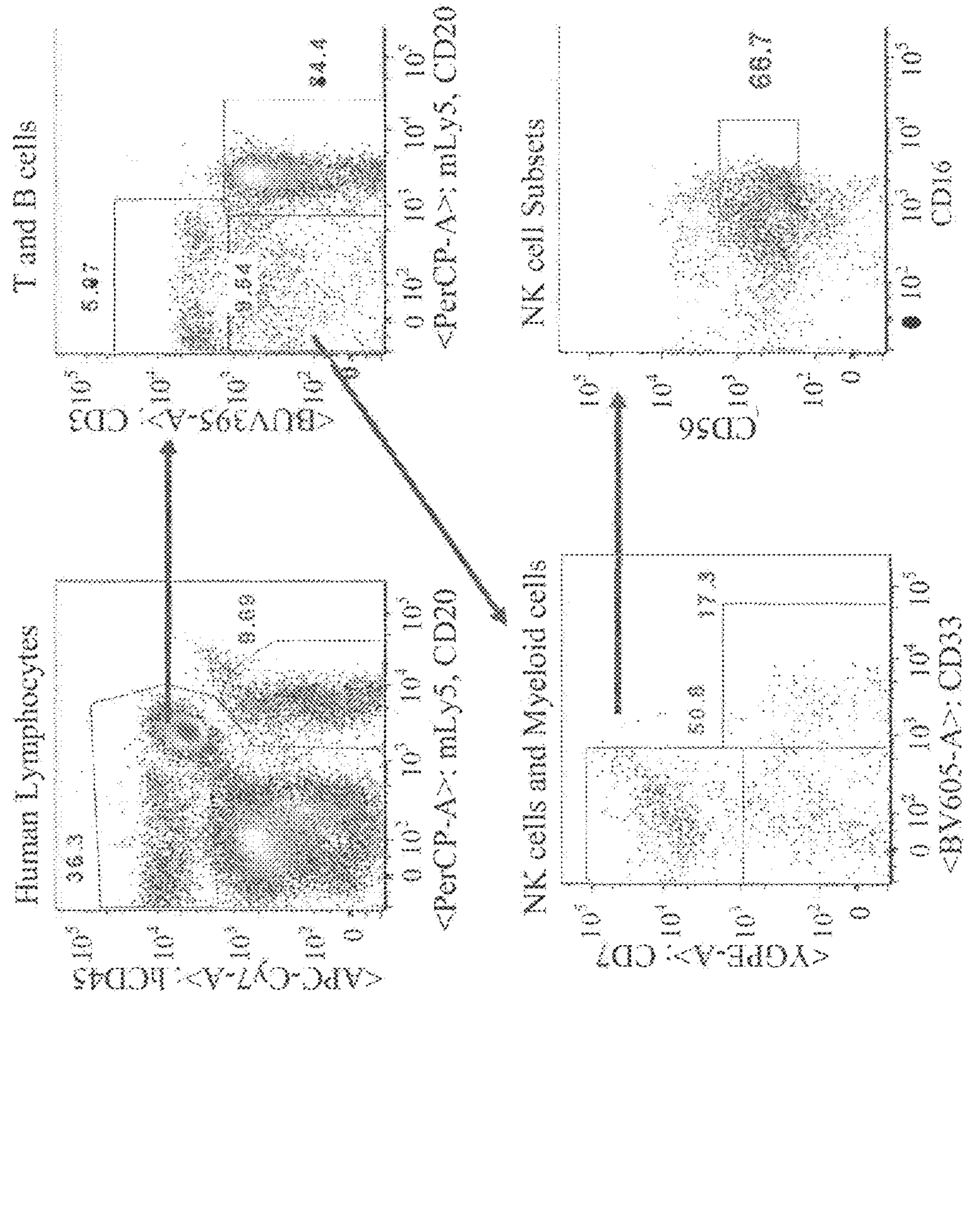
FIG. 7 shows results of flow cytometry analysis of blood cell subtypes.
Figure 8:
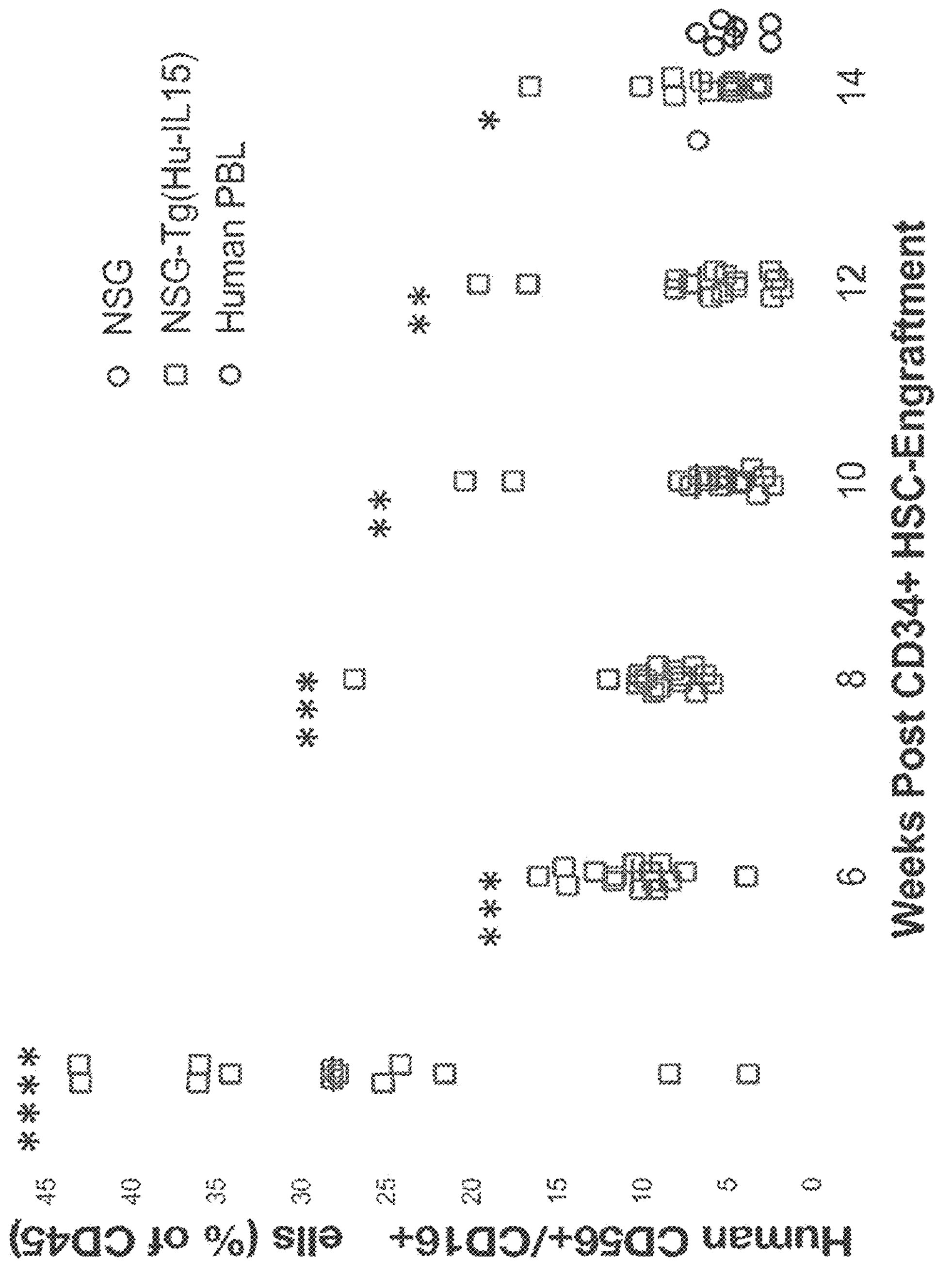
FIG. 8 is a graph showing that HSC-engrafted NSG-Tg (Hu-IL15) mice show increased human NK cell development in blood. For this study, NSG or NSG-Tg(Hu-IL15) mice (6 to 8 weeks of age) were irradiated (200 cGy) and injected IV with 100,000 CD34+ HSC derived from umbilical cord blood. Levels of human CD56+/CD16+ NK cells were monitored in the peripheral blood by flow cytometry.

Human NK cell development is significantly enhanced in HSC-engrafted NSG-Tg(Hu-IL15) mice as compared to HSC-engrafted NSG mice. Peripheral blood from HSC-engrafted mice was recovered at the indicated time points and human NK cells were detected as described in FIG. 7. Human NK cells were found at significantly higher levels at all time points tested in NSG-Tg(Hu-IL15) mice as compared to NSG mice (FIG. 8).

Figure 9:
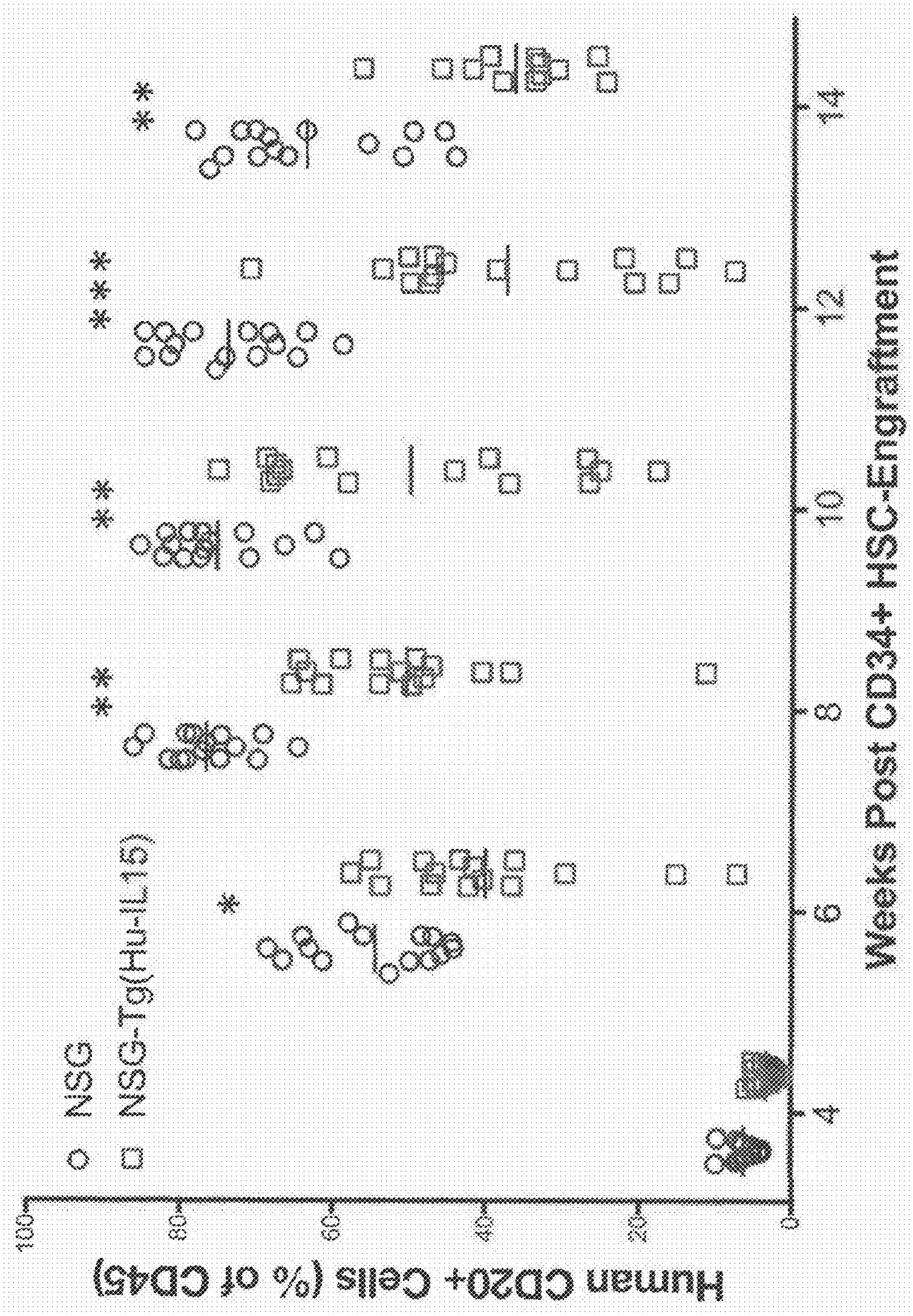
FIG. 9 is a graph showing that engrafted NSG-Tg(Hu-IL15) mice show a lower proportion of human B cells in blood. For this study, NSG or NSG-Tg(Hu-IL15) mice (6 to 8 weeks of age) were irradiated (200 cGy) and injected IV with 100,000 CD34+ HSC derived from umbilical cord blood. Levels of human CD20+ B cells were monitored in the peripheral blood by flow cytometry.

Levels of human CD20+ B cells were monitored in the peripheral blood by flow cytometry. Engrafted NSG-Tg(Hu-IL15) mice show a lower proportion of human B cells in blood compared to NSG mice, see FIG. 9.

Figure 10:
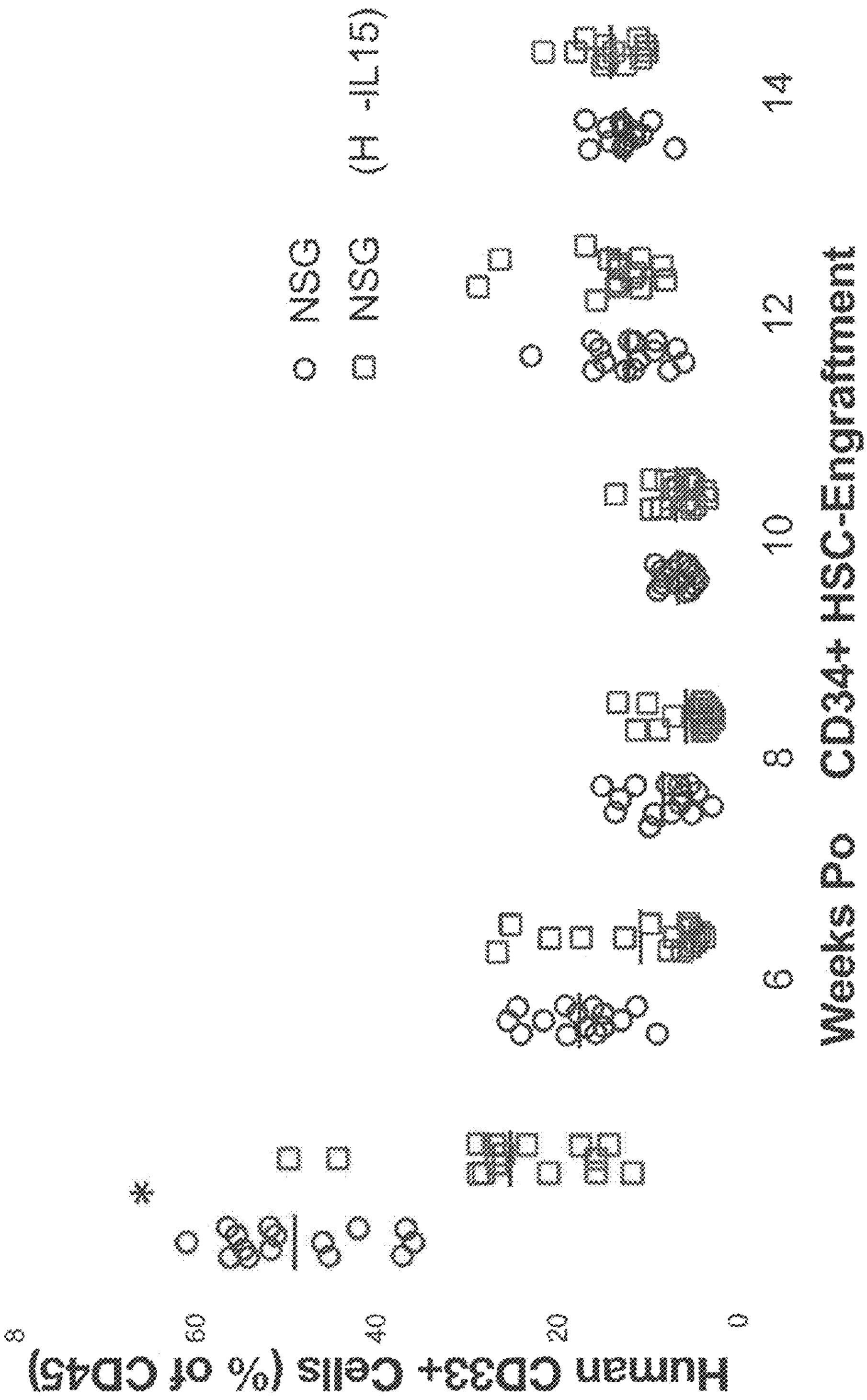
FIG. 10 is a graph showing that HSC-engrafted NSG-Tg (Hu-IL15) mice have similar development of human myeloid cells in blood. For this study, NSG or NSG-Tg(Hu-IL15) mice (6 to 8 weeks of age) were irradiated (200 cGy) and injected IV with 100,000 CD34+ HSC derived from umbilical cord blood. Levels of human CD33+ myeloid cells were monitored in the peripheral blood by flow cytometry.

Levels of human CD33+ myeloid cells were monitored in the peripheral blood by flow cytometry. HSC-engrafted NSG-Tg(Hu-IL15) mice have similar development of human myeloid cells in blood compared to NSG mice, see FIG. 10.

Figure 11:
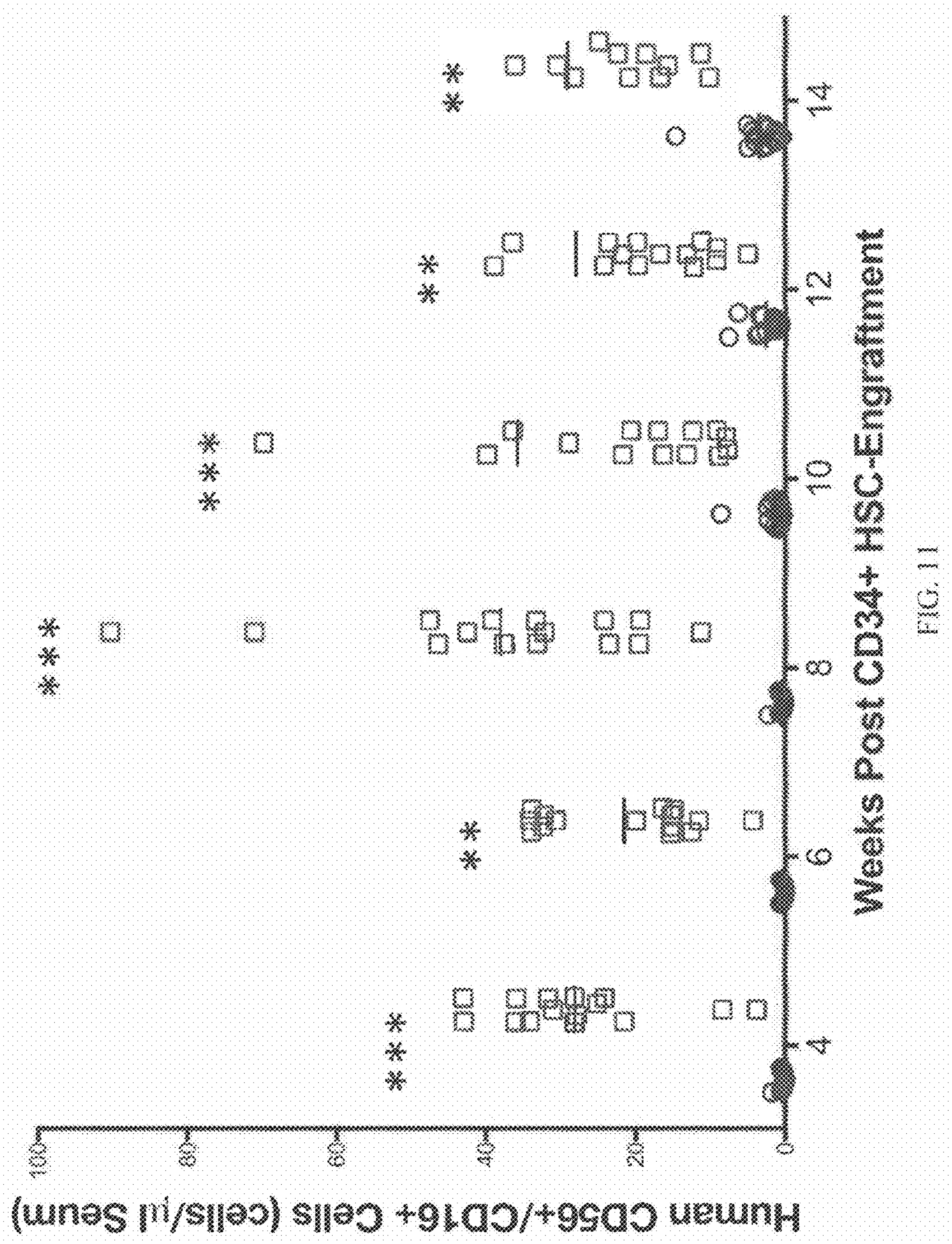
FIG. 11 is a graph showing that HSC-engrafted NSG-Tg (Hu-IL15) mice show consistent numbers of human NK cells in blood. For this study, NSG or NSG-Tg(Hu-IL15) mice (6 to 8 weeks of age) were irradiated (200 cGy) and injected IV with 100,000 CD34+ HSC derived from umbilical cord blood. Total cell levels of human CD56+/CD16+ NK cells were monitored in the peripheral blood by flow cytometry.

Total cell levels of human CD56+/CD16+ NK cells were monitored in the peripheral blood by flow cytometry. HSC-engrafted NSG-Tg(Hu-IL15) mice show consistent numbers of human NK cells in blood compared to NSG mice, see FIG. 11.

Figure 12A:
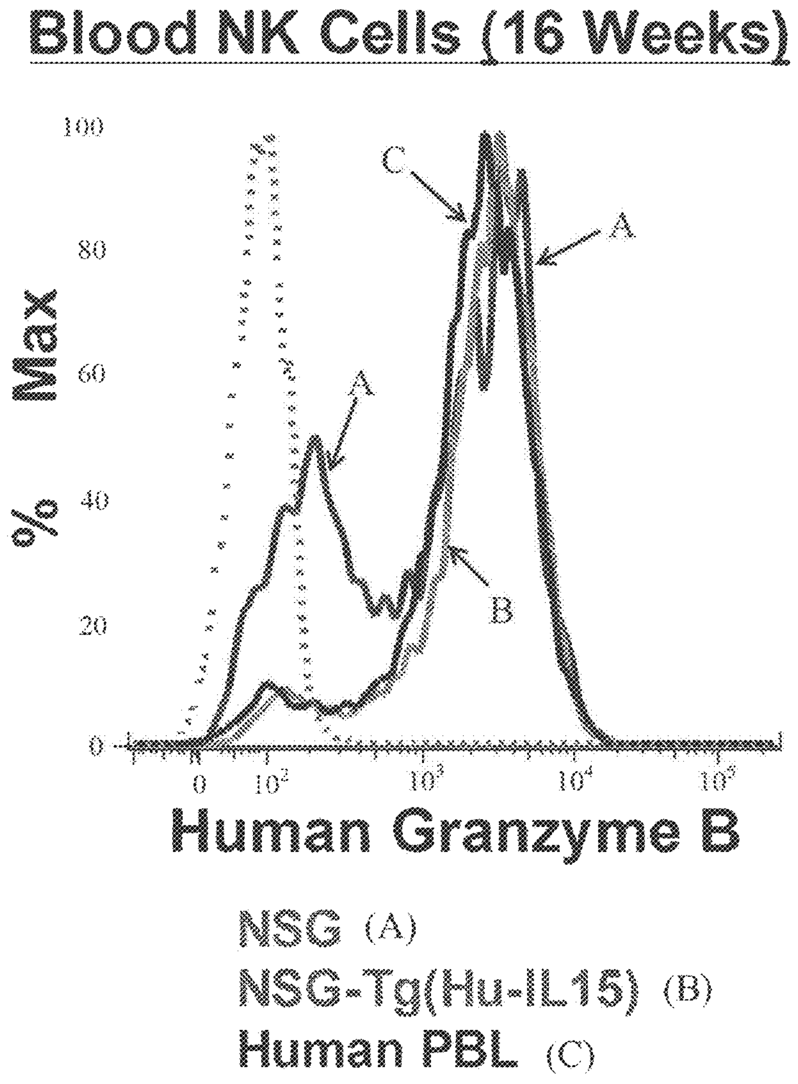
FIG. 12A is a graph showing that human NK cells from HSC-Engrafted NSG-Tg(Hu-IL15) mice express higher levels of Granzyme B. For this study, NSG or NSG-Tg(Hu-IL15) mice (6 to 8 weeks of age) were irradiated (200 cGy) and injected IV with 100,000 CD34+ HSC derived from umbilical cord blood. At 16 weeks post injection human CD56+/CD16+ NK cells were evaluated for the expression of granzyme B in blood and spleen by flow cytometry.
Figure 12B:
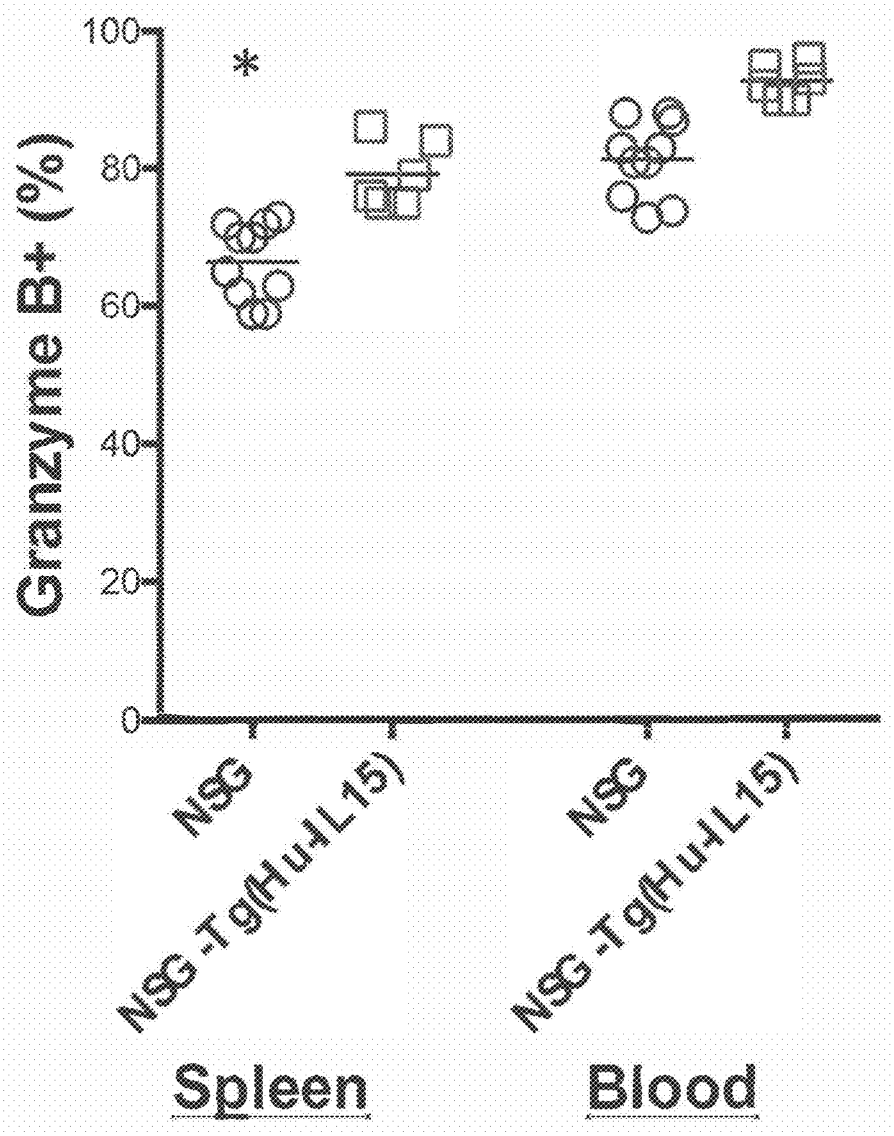
FIG. 12B is a graph showing that human NK cells from HSC-Engrafted NSG-Tg(Hu-IL15) mice express higher levels of Granzyme B. For this study, NSG or NSG-Tg(Hu-IL15) mice (6 to 8 weeks of age) were irradiated (200 cGy) and injected IV with 100,000 CD34+ HSC derived from umbilical cord blood. At 16 weeks post injection human CD56+/CD16+ NK cells were evaluated for the expression of granzyme B in blood and spleen by flow cytometry.
Figure 13A:
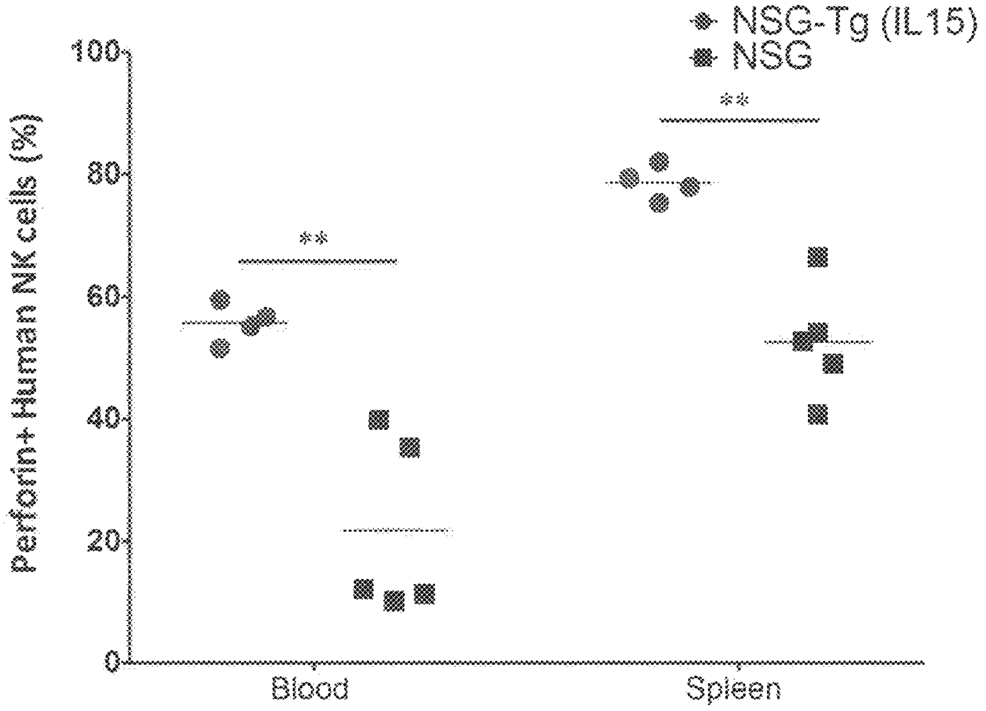
FIG. 13A is a graph showing % of perforin-positive (perforin+) NK cells in blood and spleen of NSG-Tg (IL15) mice compared to NSG mice.
Figure 13B:
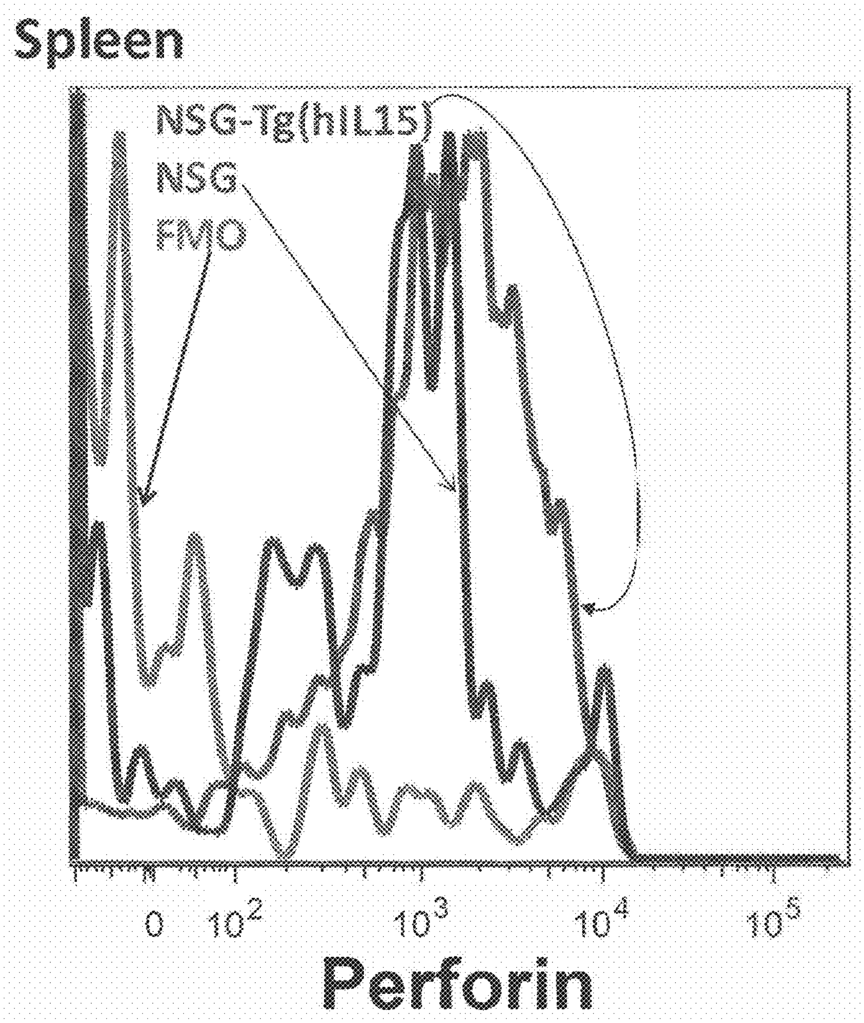
FIG. 13B is a graph showing increased expression of perforin in spleen of NSG-Tg (IL15) mice compared to NSG mice.

Human NK cells recovered from NSG-Tg(HuIL15) mice also display a functional phenotype. As shown in FIGS. 12A and 12B and FIGS. 13A and 13B, a significantly higher proportion of human NK cells in the blood and spleen of NSG-Tg(HuIL15) mice express high levels of intracellular granzyme B, a serine protease found in the granules of NK cells and intracellular perforin, a glycoprotein that is responsible for formation of pores within cell membranes. The dotted line in FIG. 12A is the curve of the "isotype controls" or "FMO" ("fluorescence minus one" control) which shows where the background level is for the cutoff for positive staining in the solid lines. It is similar to the "FMO" labeled line in FIG. 13B.

NSG-Tg(Hu-IL15) Mice Maintain Engrafted Human NK Cells

Figure 14:
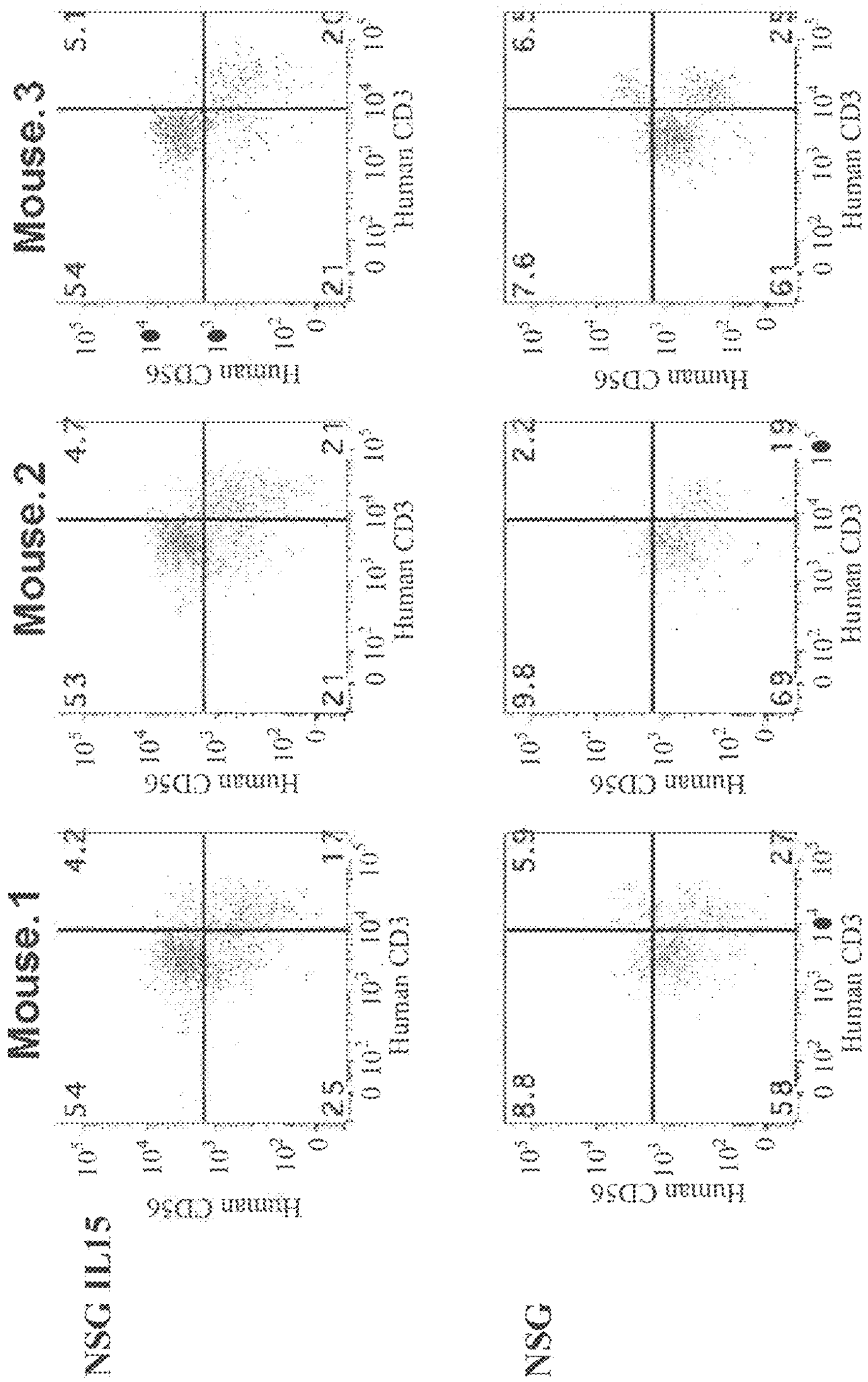
FIG. 14 shows results of flow cytometry using cells of NSG-Tg (IL15) mice and NSG mice.

In addition to the requirement for human IL-15 in supporting human NK cell development following human HSC engraftment, human NK cells require human IL-15 for survival in vivo and in vitro. In order to determine whether NSG-Tg(Hu-IL15) mice will support the maintenance of human NK cells following engraftment with human peripheral blood, groups of 8 to 12 week old NSG-Tg(Hu-IL15) mice and age and sex-matched NSG controls were engrafted with human peripheral blood mononuclear cells (1×10$^7$ PBMC) injected IV. Levels of CD56+ human NK cells were determined in the peripheral blood of injected mice at day 5. NSG-Tg(Hu-IL15) mice support enhanced engraftment and survival of human NK cells from human PBMC as compared to NSG mice. FIG. 14 shows the percentages of human CD56+ CD3− cells as a proportion of the total human CD45+ leukocytes. NSG-Tg(Hu-IL15) mice had over 50% NK cells remaining compared to less than 10% in the NSG controls.

Figure 15:
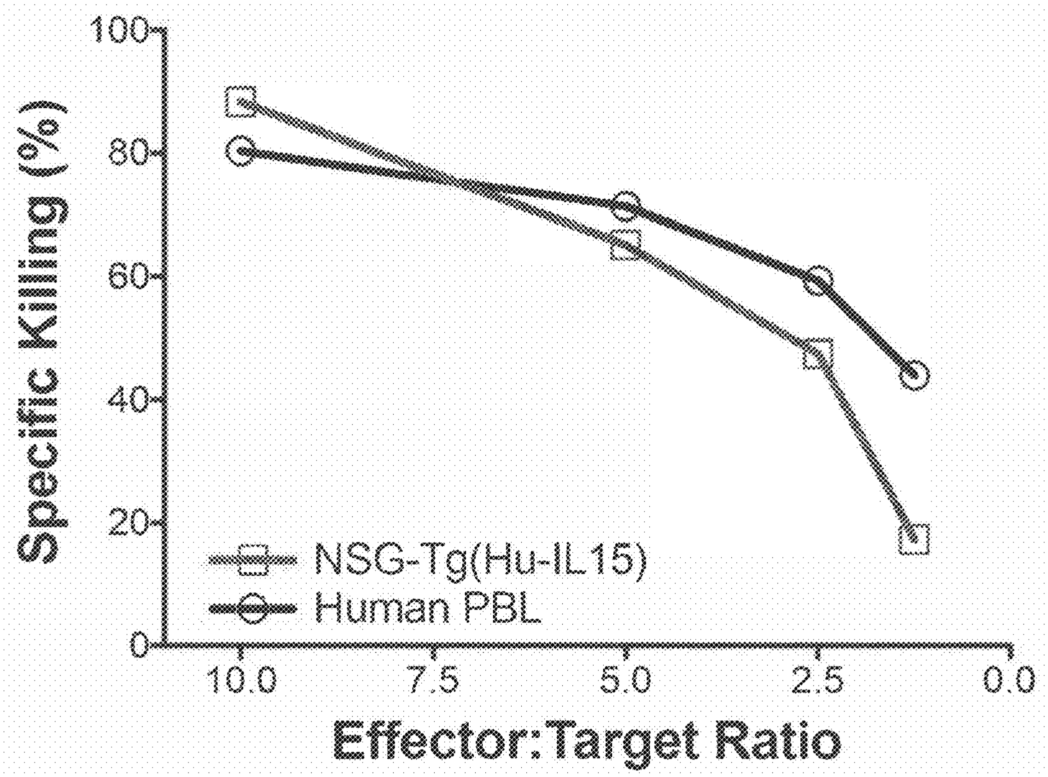
FIG. 15 is a graph showing that human NK cells from HSC-Engrafted NSG-Tg(Hu-IL15) mice kill NK sensitive targets (K562 cells). For this study, human NK cells were enriched from either the spleens of HSC-engrafted NSG-Tg (Hu-IL15) mice or human PBMC and were evaluated for the ability to lyse K562 target cells using a standard $Cr^{51}$ release assay. NK cell and K562 cells were incubated together for 20 hours and release of $Cr^{51}$ was quantified.

To determine whether human NK cells from HSC-Engrafted NSG-Tg(Hu-IL15) mice kill NK sensitive targets (K562 cells), human NK cells were enriched from either the spleens of HSC-engrafted NSG-Tg(Hu-IL15) mice or human PBMC and were evaluated for the ability to lyse K562 target cells using a standard Cr release assay. NK cell and K562 cells were incubated together for 20 hours and release of Cr was quantified. FIG. 15 is a graph showing that human NK cells from HSC-Engrafted NSG-Tg(Hu-IL15) mice kill NK sensitive targets (K562 cells).

In Vivo ADCC (Antibody Dependent Cell Mediated Cytotoxicity) Assay

NSG-IL15 mice were engrafted with human CD34+ HSC. To assess ADCC activity of the developing human NK cells, the engrafted mice and control unengrafted mice were injected subcutaneously (5 million cells) with a NK cell-sensitive B cell tumor line (CD20+, Daudi or Raji cells). When tumors became palpable mice were treated with 100 ug of anti-CD20 antibody (Rituximab) 3 times per week or left untreated. Tumor growth was monitored 2 times per week until tumor sizes reached 2000 mm$^3$ Items Item 1. An immunodeficient mouse genetically modified to include a nucleotide sequence encoding human interleukin-15 (hu-IL-15) in its genome, wherein the mouse expresses the hu-IL-15.

Item 2. The immunodeficient mouse of item 1, wherein the mouse has an absence of functional endogenous mouse NK cells.

Item 3. The immunodeficient mouse of item 1 or 2, wherein the mouse is IL-2RG null such that it lacks a functional endogenous IL-2RG gene and lacks functional endogenous mouse NK cells.

Item 4. The immunodeficient mouse of any one of the preceding items, wherein the immunodeficient mouse is a genetically modified NSG, NRG or NOG mouse.

Item 5. The immunodeficient mouse of any one of the preceding items, further comprising human hematopoietic stem cells, human peripheral blood mononuclear cells (PBMCs), human NK cells, human NK cell line cells, or a combination of any two or more thereof.

Item 6. The immunodeficient mouse of any one of the preceding items, wherein the mouse comprises human natural killer cells and the human natural killer cells are produced in the mouse by differentiation of human hematopoietic stem cells in the mouse or wherein the human natural killer cells are maintained and/or produced in the mouse following administration of PBMCs containing human natural killer cells.

Item 7. The immunodeficient mouse of any one of the preceding items, further comprising a human xenograft comprising human tumor cells.

Item 8. A method of identifying anti-tumor activity of a test substance, comprising: providing an immunodeficient mouse according to any one of items 1 to 6; administering human tumor cells to the immunodeficient mouse, wherein the human tumor cells form a solid or non-solid tumor in the genetically-modified, immunodeficient mouse; administering a test substance to the immunodeficient mouse; and assaying a response of the solid or non-solid tumor to the test substance, wherein an inhibitory effect of the test substance on the tumor and/or tumor cells identifies the test substance as having anti-tumor activity.

Item 9. The method of item 8, further comprising comparing the response to a standard to determine the effect of the test substance on the human tumor cells, wherein an inhibitory effect of the test substance on the human tumor cells identifies the test substance as having anti-tumor activity.

Item 10. The method of item 8 or 9, wherein the test substance comprises an immunotherapeutic agent.

Item 11. The method of any one of items 8 to 10, wherein the test substance is an immune checkpoint inhibitor.

Item 12. The method of item 11, wherein the immune checkpoint inhibitor is a PD-1 inhibitor, PD-L1 inhibitor, or CTLA-4 inhibitor.

Item 13. The method of item 11 or 12, wherein the immune checkpoint inhibitor is atezolizumab, avelumab, durvalumab, ipilimumab, nivolumab, or pembrolizumab, or the immune checkpoint inhibitor comprises an antigen-binding fragment of any one of the foregoing.

Item 14. The method of any one of items 8 to 13, wherein the test substance comprises an antibody.

Item 15. The method of any one of items 8 to 14, wherein the test substance comprises an anti-cancer agent.

Item 16. A method of making a genetically-modified, immunodeficient humanized mouse model, comprising: providing an immunodeficient mouse according to any one of items 1 to 4; and administering human hematopoietic stem cells, human peripheral blood mononuclear cells (PBMCs), human NK cells, human NK cell line cells, or a combination of any two or more thereof, to the immunodeficient mouse.

Item 17. The method of item 16, further comprising conditioning the immunodeficient mouse to reduce mouse hematopoietic cells of the mouse prior to administering human hematopoietic stem cells, human peripheral blood mononuclear cells (PBMCs), human NK cells, human NK cell line cells, or a combination of any two or more thereof.

Item 18. The method of item 17, wherein conditioning the immunodeficient mouse to reduce mouse hematopoietic cells of the mouse comprises irradiating the genetically-modified, immunodeficient mouse and/or administering a radiomimetic drug to the genetically-modified, immunodeficient mouse.

Item 19. The method of item 18, wherein no conditioning to reduce mouse hematopoietic cells of the mouse is performed prior to administering human hematopoietic stem cells.

Item 20. The method of any one of items 16 to 19, further comprising administering a human xenograft comprising human tumor cells to the immunodeficient mouse.

Item 21. A genetically-modified, immunodeficient mouse substantially as described or shown herein.

Item 22. A method of making a genetically-modified, immunodeficient humanized mouse model substantially as described or shown herein.

Item 23. A method of identifying anti-tumor activity of a test substance substantially as described or shown herein.

Sequences

```
Human Interleukin 15
                                           SEQ ID NO: 1
MRISKPHLRSISIQCYLCLLLNSHFLTEAGIHVFILGCFSAGLPKTEAN

WVNVISDLKKIEDLIQSMHIDATLYTESDVHPSCKVTAMKCFLLELQVI

SLESGDASIHDTVENLIILANNSLSSNGNVTESGCKECEELEEKNIKEF

LQSFVHIVQMFINTS

Encoding Human Interleukin 15
                                           SEQ ID NO: 2
atgagaatttcgaaaccacatttgagaagtatttccatccagtgctact

tgtgtttacttctaaacagtcattttctaactgaagctggcattcatgt

cttcattttgggctgtttcagtgcagggcttcctaaaacagaagccaac

tgggtgaatgtaataagtgatttgaaaaaaattgaagatcttattcaat

ctatgcatattgatgctactttatatacggaaagtgatgttcaccccag

ttgcaaagtaacagcaatgaagtgctttctcttggagttacaagttatt

tcacttgagtccggagatgcaagtattcatgatacagtagaaaatctga

tcatcctagcaaacaacagtttgtcttctaatgggaatgtaacagaatc

tggatgcaaagaatgtgaggaactggaggaaaaaaatattaaagaattt

ttgcagagttttgtacatattgtccaaatgttcatcaacacttct
```

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination.

Any patents or publications mentioned in this specification are incorporated herein by reference to the same extent as if each individual publication is specifically and individually indicated to be incorporated by reference.

The compositions and methods described herein are presently representative of preferred embodiments, exemplary, and not intended as limitations on the scope of the invention. Changes therein and other uses will occur to those skilled in the art. Such changes and other uses can be made without departing from the scope of the invention as set forth in the claims.

The invention claimed is:

1. A method of identifying anti-tumor activity of a test substance, comprising:

(a) administering a test substance to an immunodeficient non-obese diabetic mouse whose genome (i) comprises a null mutation in a Prkdc gene, a null mutation in a IL2rγ gene, and a human interleukin-15 transgene, and (ii) expresses human interleukin-15, wherein the immunodeficient non-obese diabetic mouse comprises human tumor cells and human natural killer cells; and (b) assaying the immunodeficient non-obese diabetic mouse for an effect of the test substance on the human tumor cells.

2. The method of claim 1, wherein the test substance comprises an anti-cancer agent.

3. The method of claim 2, wherein the test substance comprises an antibody.

4. The method of claim 2, wherein the test substance comprises an immunotherapeutic.

5. The method of claim 4, wherein the immunotherapeutic is an immune checkpoint inhibitor.

6. The method of claim 5, wherein the immune checkpoint inhibitor is a PD-1 inhibitor, PD-L1 inhibitor, or CTLA-4 inhibitor.

7. The method of claim 6, wherein the immune checkpoint inhibitor is atezolizumab, avelumab, durvalumab, ipilimumab, nivolumab, pembrolizumab, or an antigen-binding fragment of any one of the foregoing.

8. The method of claim 1, wherein the effect is an inhibitory effect.

9. The method of claim 1, wherein the immunodeficient non-obese diabetic mouse has been engrafted with human hematopoietic stem cells or human peripheral blood mononuclear cells.

10. A method of identifying anti-tumor activity of a test substance, comprising:

(a) administering human tumor cells to an immunodeficient non-obese diabetic mouse whose genome (i) comprises a null mutation in a Prkdc gene, a null mutation in a IL2rγ gene, and a human interleukin-15 transgene, and (ii) expresses human interleukin-15, wherein the immunodeficient non-obese diabetic mouse comprises human natural killer cells;

(b) administering a test substance to the immunodeficient non-obese diabetic mouse; and (c) assaying the immunodeficient non-obese diabetic mouse for an effect of the test substance on the human tumor cells.

11. The method of claim 10, wherein the test substance comprises an anti-cancer agent.

12. The method of claim 11, wherein the test substance comprises an antibody.

13. The method of claim 11, wherein the test substance comprises an immunotherapeutic.

14. The method of claim 13, wherein the immunotherapeutic is an immune checkpoint inhibitor.

15. The method of claim 14, wherein the immune checkpoint inhibitor is a PD-1 inhibitor, PD-L1 inhibitor, or CTLA-4 inhibitor.

16. The method of claim 15, wherein the immune checkpoint inhibitor is atezolizumab, avelumab, durvalumab, ipilimumab, nivolumab, pembrolizumab, or an antigen-binding fragment of any one of the foregoing.

17. The method of claim 10, wherein the effect is an inhibitory effect.

18. The method of claim 10, wherein the immunodeficient non-obese diabetic mouse has been engrafted with human hematopoietic stem cells or human peripheral blood mononuclear cells.

19. A method of identifying anti-tumor activity of a test substance, comprising:

(a) irradiating an immunodeficient non-obese diabetic mouse whose genome (i) comprises a null mutation in a Prkdc gene, a null mutation in a IL2rγ gene, and a human interleukin-15 transgene, and (ii) expresses human interleukin-15;

(b) administering human hematopoietic stem cells or human peripheral blood mononuclear cells to the immunodeficient non-obese diabetic mouse to produce human natural killer cells;

(c) administering human tumor cells to the immunodeficient non-obese diabetic mouse; and (d) assaying the immunodeficient non-obese diabetic mouse for an effect of the test substance on the human tumor cells.

20. The method of claim 19, wherein the test substance is an immunotherapeutic.

* * * * *

SEQUENCE LISTING

```
Sequence total quantity: 2
SEQ ID NO: 1            moltype = AA  length = 162
FEATURE                 Location/Qualifiers
source                  1..162
                        mol_type = protein
                        organism = Homo sapiens
SEQUENCE: 1
MRISKPHLRS ISIQCYLCLL LNSHFLTEAG IHVFILGCFS AGLPKTEANW VNVISDLKKI  60
EDLIQSMHID ATLYTESDVH PSCKVTAMKC FLLELQVISL ESGDASIHDT VENLIILANN  120
SLSSNGNVTE SGCKECEELE EKNIKEFLQS FVHIVQMFIN TS                      162
```

-continued

```
SEQ ID NO: 2            moltype = DNA  length = 486
FEATURE                 Location/Qualifiers
source                  1..486
                        mol_type = genomic DNA
                        organism = Homo sapiens
SEQUENCE: 2
atgagaattt cgaaaccaca tttgagaagt atttccatcc agtgctactt gtgtttactt  60
ctaaacagtc attttctaac tgaagctggc attcatgtct tcattttggg ctgtttcagt  120
gcagggcttc ctaaaacaga agccaactgg gtgaatgtaa taagtgattt gaaaaaaatt  180
gaagatctta ttcaatctat gcatattgat gctactttat atacggaaag tgatgttcac  240
cccagttgca aagtaacagc aatgaagtgc tttctcttgg agttacaagt tatttcactt  300
gagtccggag atgcaagtat tcatgataca gtagaaaatc tgatcatcct agcaaacaac  360
agtttgtctt ctaatgggaa tgtaacagaa tctggatgca aagaatgtga ggaactggag  420
gaaaaaaata ttaaagaatt tttgcagagt tttgtacata ttgtccaaat gttcatcaac  480
acttct                                                             486
```